United States Patent [19]
Yoon

[11] Patent Number: 5,707,362
[45] Date of Patent: Jan. 13, 1998

[54] PENETRATING INSTRUMENT HAVING AN EXPANDABLE ANCHORING PORTION FOR TRIGGERING PROTRUSION OF A SAFETY MEMBER AND/OR RETRACTION OF A PENETRATING MEMBER

[76] Inventor: InBae Yoon, 2101 Highland Ridge Dr., Phoenix, Md. 20850

[21] Appl. No.: 417,046

[22] Filed: Apr. 3, 1995

Related U.S. Application Data

[60] Continuation-in-part of Ser. No. 79,586, Jun. 22, 1993, Pat. No. 5,423,770, which is a division of Ser. No. 868,578, Apr. 15, 1992, Pat. No. 5,336,176.

[51] Int. Cl.⁶ .................................................. A61M 25/00
[52] U.S. Cl. ............................................ 604/164; 604/175
[58] Field of Search ............................... 604/104, 105, 604/106, 107, 109, 164, 175

[56] References Cited

U.S. PATENT DOCUMENTS

| | | |
|---|---|---|
| Re. 32,922 | 5/1989 | Levin et al. . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 3,039,468 | 6/1962 | Price ........................... 604/107 X |
| 3,397,699 | 8/1968 | Kohl ................................. 604/105 |
| 3,680,562 | 8/1972 | Wittes et al. . |
| 4,254,762 | 3/1981 | Yoon . |
| 4,345,589 | 8/1982 | Hiltebrandt . |
| 4,393,873 | 7/1983 | Nawash et al. . |
| 4,442,836 | 4/1984 | Meinecke et al. . |
| 4,488,544 | 12/1984 | Shen . |
| 4,503,856 | 3/1985 | Cornell et al. . |
| 4,535,773 | 8/1985 | Yoon . |
| 4,559,041 | 12/1985 | Razi . |
| 4,601,710 | 7/1986 | Moll . |
| 4,608,965 | 9/1986 | Anspach, Jr. et al. . |
| 4,627,841 | 12/1986 | Dorr . |
| 4,654,030 | 3/1987 | Moll et al. . |
| 4,670,008 | 6/1987 | Von Albertini . |
| 4,677,979 | 7/1987 | Burns . |
| 4,747,831 | 5/1988 | Kulli . |
| 4,817,603 | 4/1989 | Turner et al. . |
| 4,820,275 | 4/1989 | Haber et al. . |
| 4,869,717 | 9/1989 | Adair . |
| 4,889,117 | 12/1989 | Stevens . |
| 4,900,307 | 2/1990 | Kulli . |
| 4,902,280 | 2/1990 | Lander . |
| 4,906,236 | 3/1990 | Alberts et al. . |
| 4,931,042 | 6/1990 | Holmes et al. . |
| 4,943,280 | 7/1990 | Lander . |
| 4,946,446 | 8/1990 | Vadher . |
| 4,955,870 | 9/1990 | Ridderheim et al. . |
| 4,966,593 | 10/1990 | Lennox . |
| 4,973,316 | 11/1990 | Dysarz . |
| 4,986,814 | 1/1991 | Burney et al. . |
| 4,994,042 | 2/1991 | Vadher . |
| 4,994,068 | 2/1991 | Hufnagle . |
| 5,024,665 | 6/1991 | Kaufman . |
| 5,026,388 | 6/1991 | Inqaiz . |
| 5,030,206 | 7/1991 | Lander . |

(List continued on next page.)

FOREIGN PATENT DOCUMENTS

| | | |
|---|---|---|
| 2544262 | 4/1977 | Germany . |
| 1435246 | 11/1988 | U.S.S.R. . |

*Primary Examiner*—Sam Rimell

[57] ABSTRACT

A penetrating instrument for penetrating a wall of an anatomical cavity to gain access to the anatomical cavity includes a fixed or retractable penetrating member having a distal end for penetrating the anatomical cavity wall, a portal sleeve or a distally biased safety member having a distal end movable between an extended position protecting the distal end of the penetrating member and a retracted position exposing the distal end of the penetrating member, and an expandable portion carried by the penetrating instrument and being movable from an expanded position to a contracted position during penetration of the cavity wall and from the contracted position to the expanded position upon introduction of the expandable portion in the anatomical cavity to anchor the portal sleeve relative to the anatomical cavity wall and/or to trigger extension of the safety member and/or retraction of the penetrating member.

21 Claims, 13 Drawing Sheets

U.S. PATENT DOCUMENTS

| | | |
|---|---|---|
| 5,053,016 | 10/1991 | Lander . |
| 5,061,251 | 10/1991 | Juhasz . |
| 5,066,288 | 11/1991 | Deniega et al. . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,122,122 | 6/1992 | Allgood . |
| 5,127,909 | 7/1992 | Shichman . |
| 5,147,316 | 9/1992 | Castillenti . |
| 5,152,754 | 10/1992 | Plyley . |
| 5,158,552 | 10/1992 | Borgia et al. . |
| 5,183,033 | 2/1993 | Wilk . |
| 5,203,773 | 4/1993 | Green . |
| 5,207,647 | 5/1993 | Phelps . |
| 5,217,451 | 6/1993 | Freitas . |
| 5,224,930 | 7/1993 | Spaeth et al. ........................ 604/164 X |
| 5,232,440 | 8/1993 | Wilk . |
| 5,248,302 | 9/1993 | Patrick et al. . |
| 5,257,975 | 11/1993 | Foshee . |
| 5,282,788 | 2/1994 | Wilk et al. . |
| 5,290,243 | 3/1994 | Chodorow et al. . |
| 5,290,304 | 3/1994 | Storace . |
| 5,295,993 | 3/1994 | Green . |
| 5,312,354 | 5/1994 | Allen et al. . |
| 5,318,012 | 6/1994 | Wilk . |
| 5,318,580 | 6/1994 | Gresl, Jr. . |
| 5,318,585 | 6/1994 | Guy et al. . |
| 5,320,610 | 6/1994 | Yoon . |
| 5,324,268 | 6/1994 | Yoon . |
| 5,330,497 | 7/1994 | Freitas et al. . |
| 5,342,382 | 8/1994 | Brinkerhoff et al. . |
| 5,372,588 | 12/1994 | Farley et al. .............................. 604/164 |
| 5,387,196 | 2/1995 | Green et al. . |
| 5,399,167 | 3/1995 | Deniega et al. ....................... 604/164 |
| 5,419,777 | 5/1995 | Hofling ................................ 604/164 X |
| 5,512,053 | 4/1996 | Pearson et al. ..................... 604/164 X |

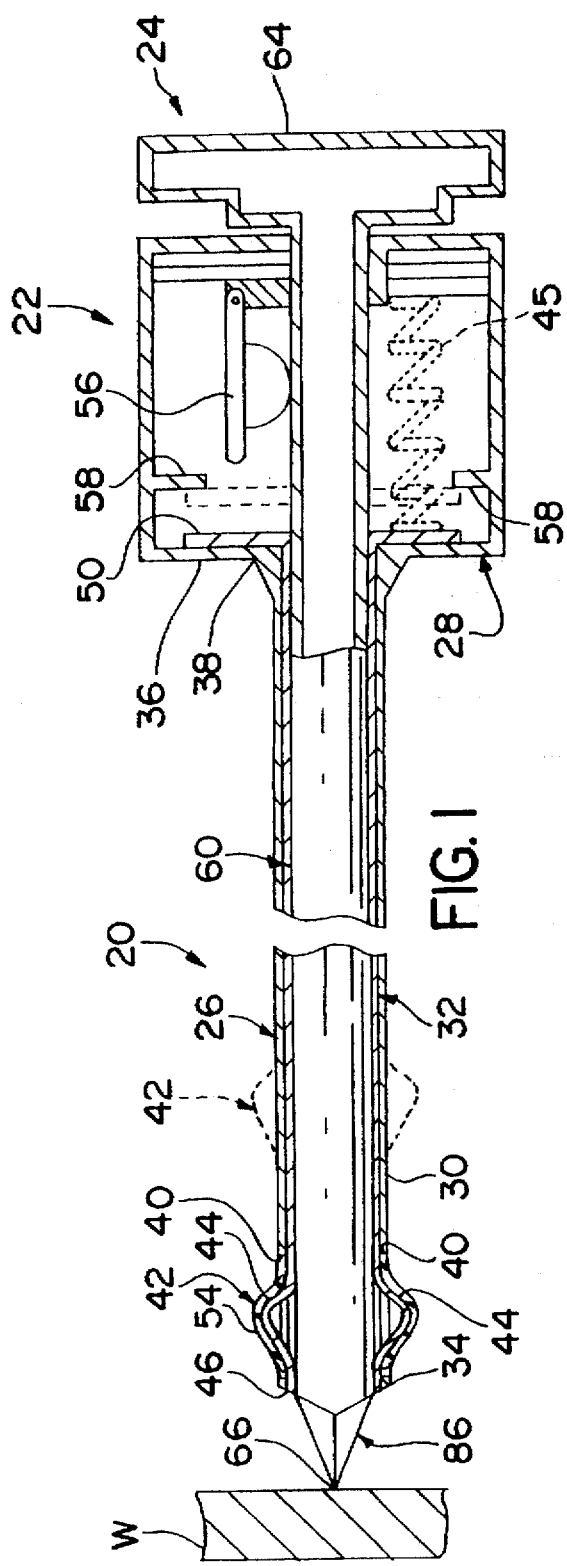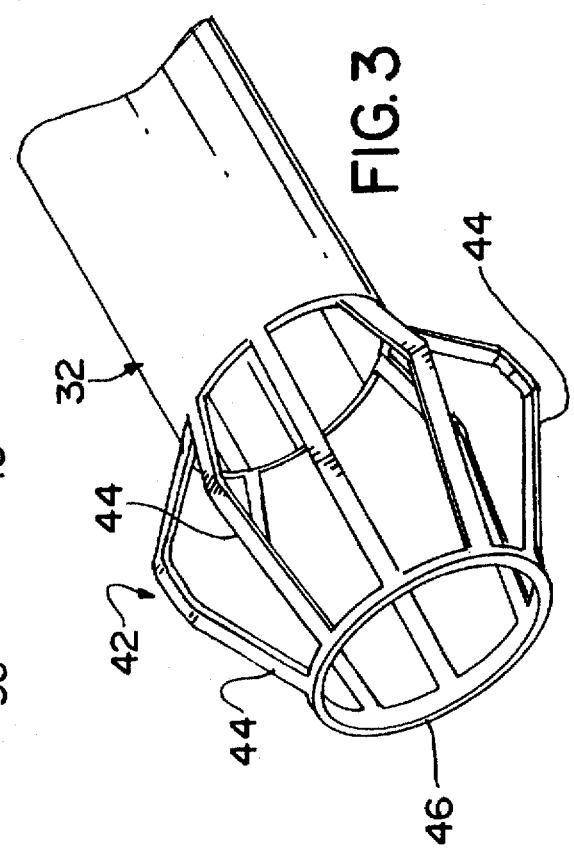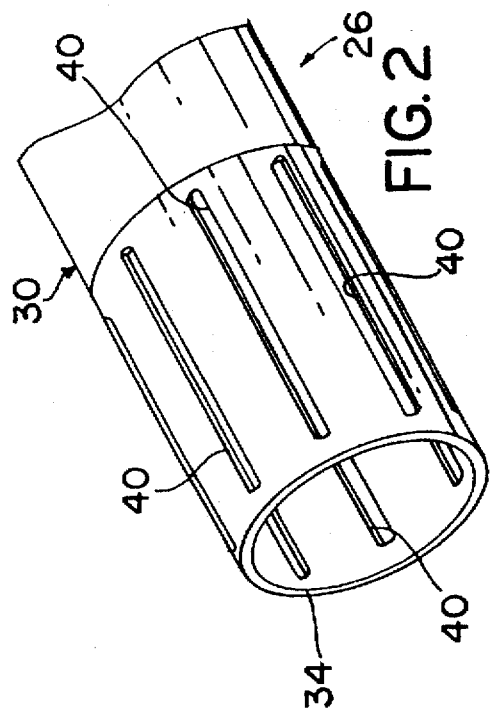

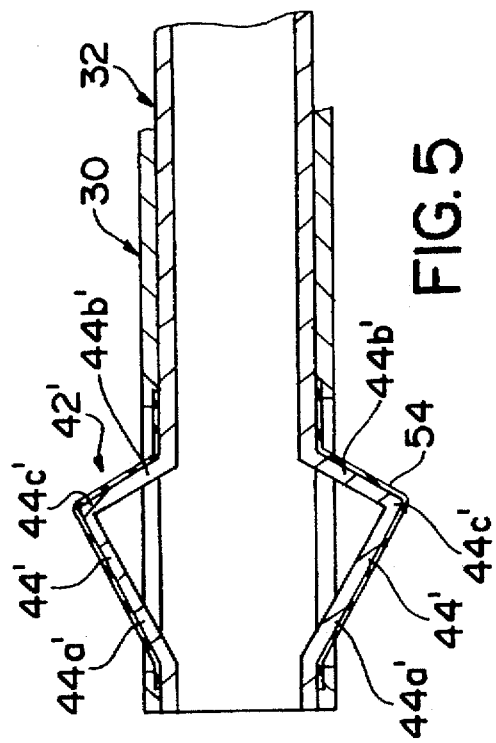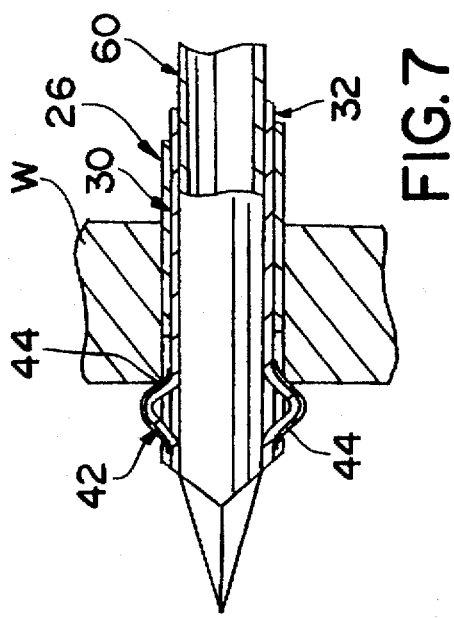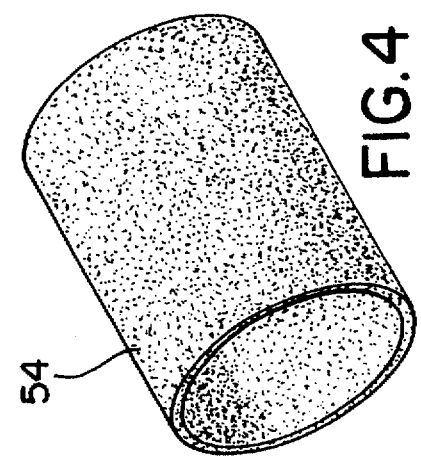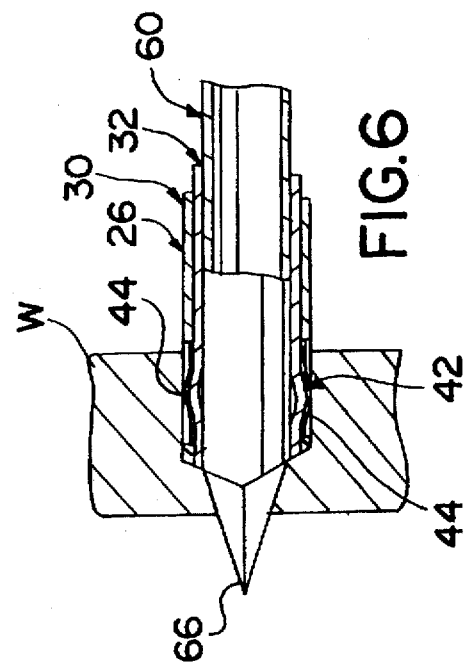

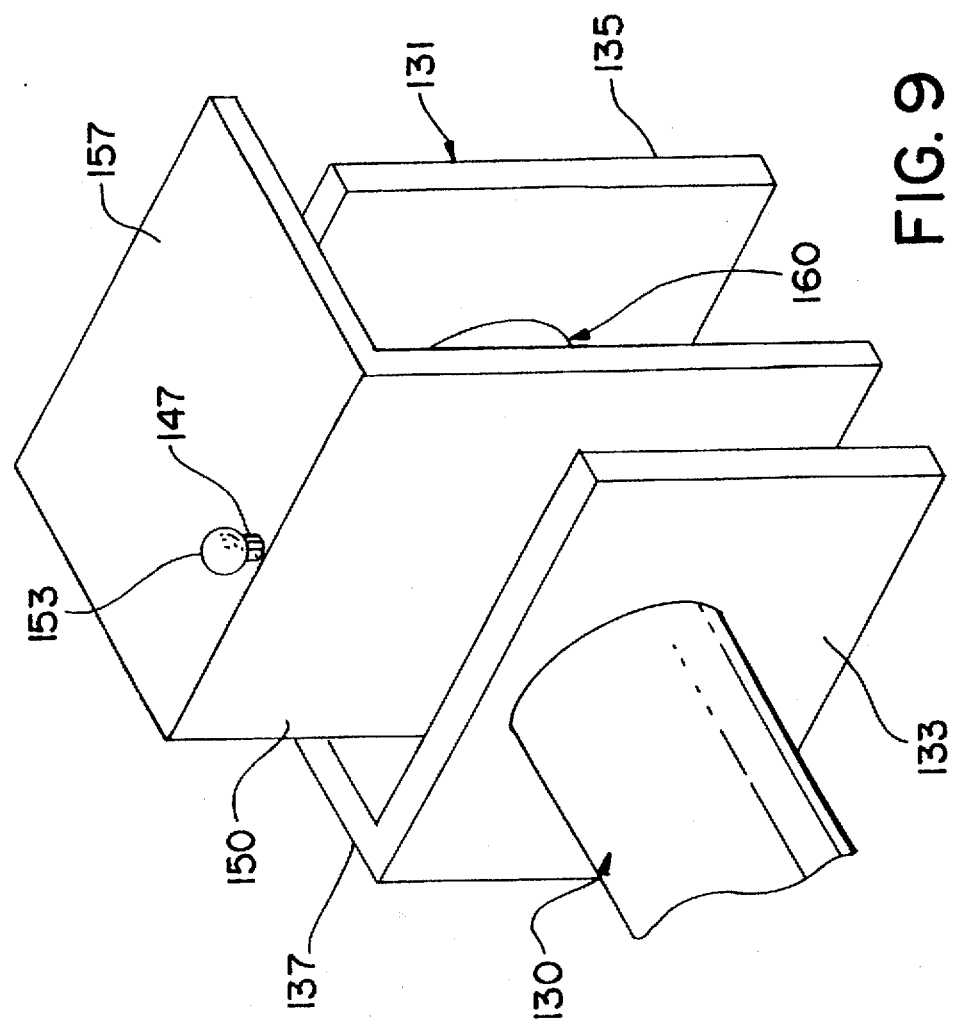

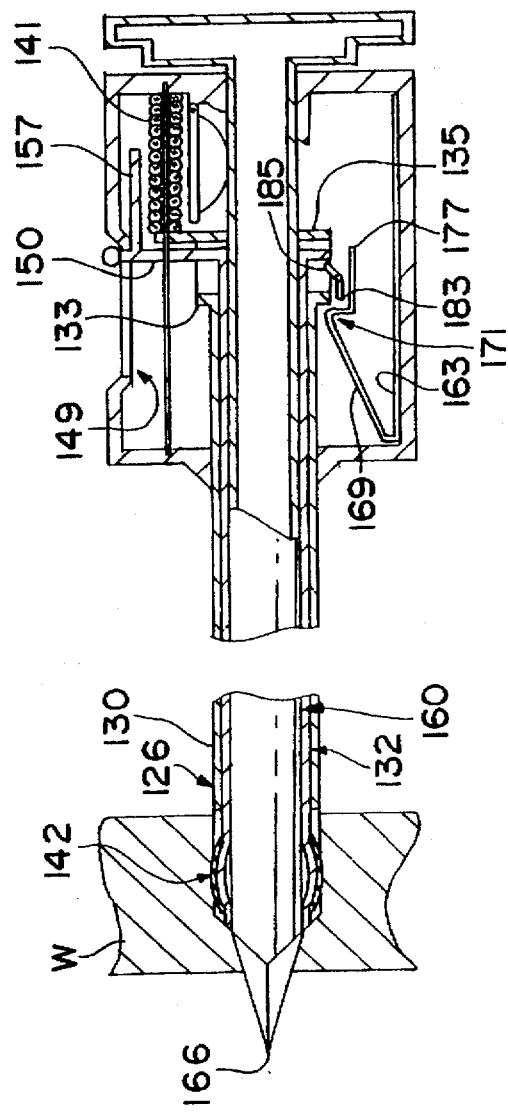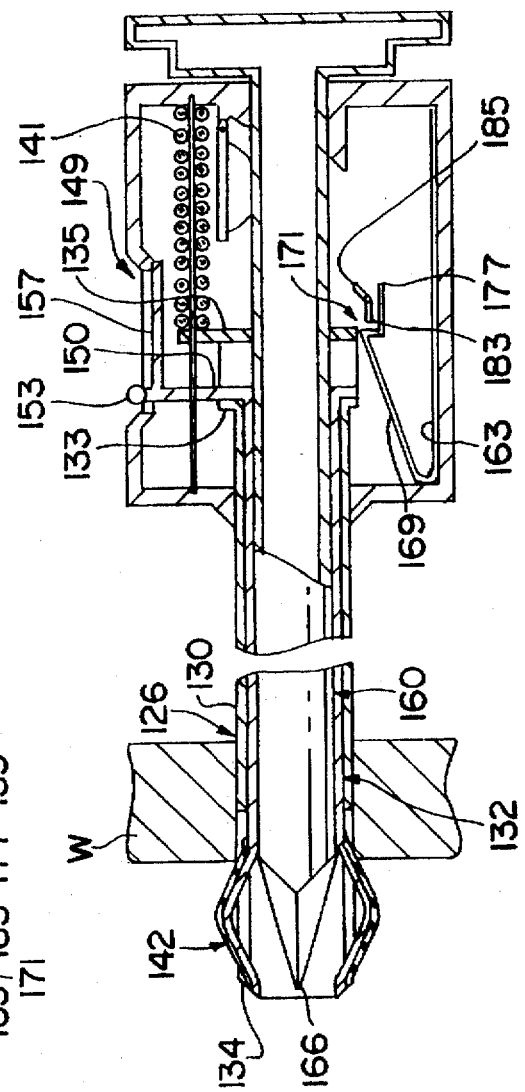

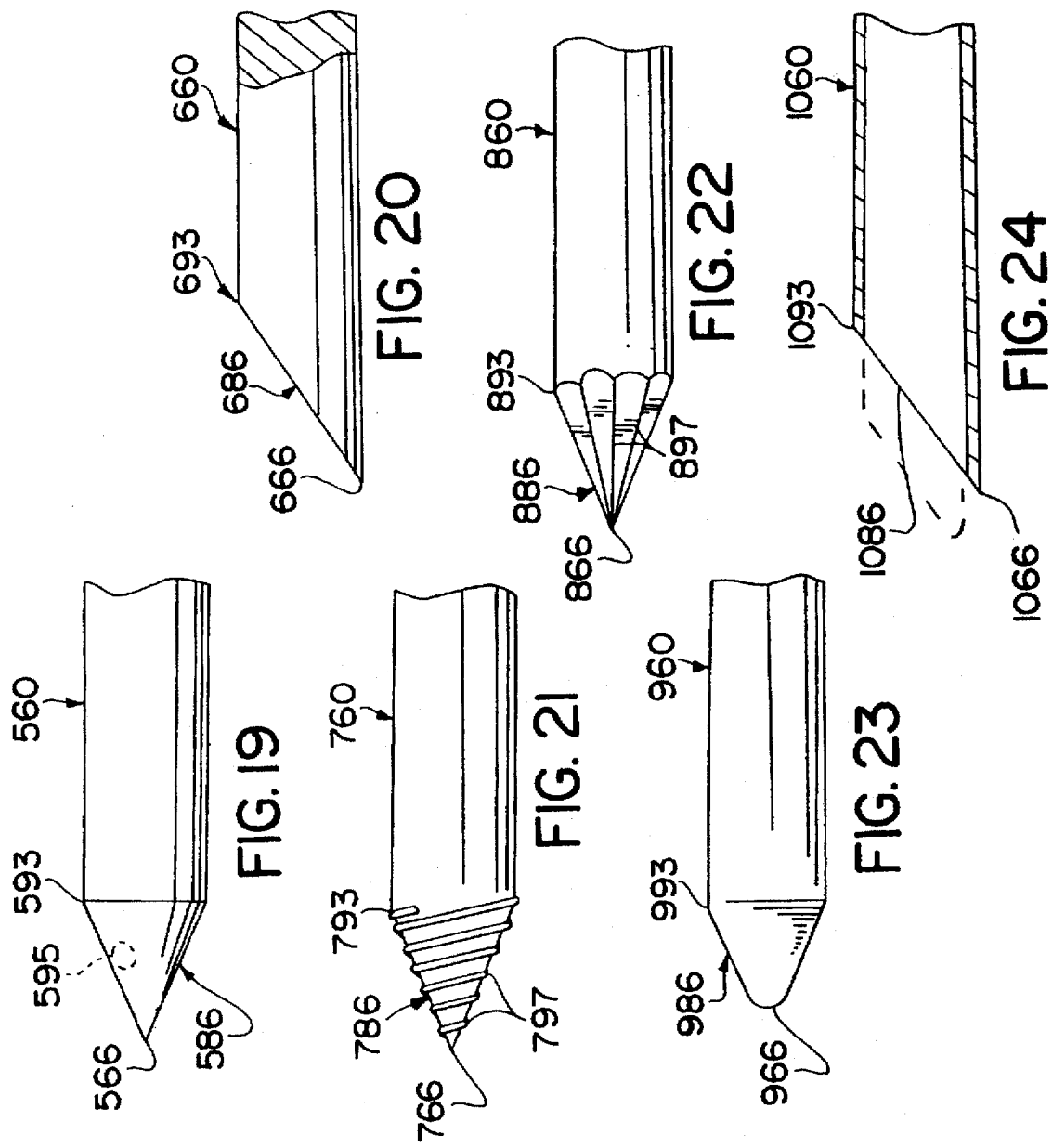

PENETRATING INSTRUMENT HAVING AN EXPANDABLE ANCHORING PORTION FOR TRIGGERING PROTRUSION OF A SAFETY MEMBER AND/OR RETRACTION OF A PENETRATING MEMBER

CROSS-REFERENCE TO RELATED APPLICATIONS

This application is a continuation-in-part of application Ser. No. 08/079,586, filed Jun. 22, 1993 now U.S. Pat. No. 5,423,770, which is a division of application Ser. No. 07/868,578, filed Apr. 15, 1992, now U.S. Pat. No. 5,336, 176, the disclosures of which are incorporated herein by reference.

BACKGROUND OF THE INVENTION

1. Field of the Invention

The present invention pertains to penetrating instruments for penetrating walls of anatomical cavities and, more particularly, to penetrating instruments having retractable penetrating members and/or safety members biased to an extended protruding position such that tissue and organ structures are protected from the tips of the penetrating members. The present invention also pertains to penetrating instruments having anchoring members to automatically anchor the penetrating instruments upon penetration into anatomical cavities.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or minimally invasive, surgery to establish an endoscopic portal for many various procedures, such as laproscopic procedures in the abdominal cavity. Such penetrating instruments typically include a cannula or portal sleeve and a penetrating member, such as a trocar, disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring-biased to protrude axially beyond the tip of the penetrating member in response to the reduced force on the distal end of the safety member upon entry into the anatomical cavity. The safety member can be disposed around the penetrating member in which case the safety member is frequently referred to as a shield, or the safety member can be disposed within the penetrating member in which case the safety member is frequently referred to as a probe. In retracting safety penetrating instruments, the penetrating member is retracted into the cannula upon entry into the anatomical cavity in response to distal movement of a component of the safety penetrating instrument such as the penetrating member, the cannula, a probe or a safety member such as a shield or probe.

While safety penetrating instruments have been well received, there is room for improvement in minimizing the likelihood of a safety member being extended or a penetrating member being retracted before the cannula has entered the anatomical cavity in that distal movement of a triggering component of the safety penetrating instrument can be induced prematurely if the axial penetrating force applied by the surgeon is irregular or uneven.

Penetrating instruments for establishing communication with anatomical cavities in many various medical procedures and having anchoring members for anchoring the penetrating instruments relative to the anatomical cavities have also been proposed. However, there is room for improvement in this area as well due to the need for intervention by the surgeon to actuate the anchoring members upon penetration into the anatomical cavities.

SUMMARY OF THE INVENTION

Accordingly, it is a primary object of the present invention to improve penetrating instruments of the type having anchoring members for anchoring the penetrating instruments upon penetration by the penetrating instruments into anatomical cavities.

Another object of the present invention is to utilize an expandable portion of a penetrating instrument as an anchoring member for anchoring the penetrating instrument relative to an anatomical cavity wall upon penetration of the penetrating instrument into the anatomical cavity.

A further object of the present invention is to carry or form an expandable member on a penetrating instrument and permit movement of the expandable portion from an expanded position to a contracted position automatically in response to resistance from anatomical tissue during penetration and from the contracted position to the expanded position upon introduction of the expandable portion in the anatomical cavity.

The present invention has as an additional object to utilize lateral movement of an expandable portion of a penetrating instrument from a contracted position to an expanded anchoring position to trigger movement of a safety member to an extended protruding position protecting the tip of a penetrating member and/or proximal movement of the penetrating member to a retracted position where the tip of the penetrating member is protected.

Some of the advantages of the present invention are that anchoring of a penetrating instrument relative to an anatomical cavity wall can be achieved without the need for intervention by the surgeon to actuate the anchoring member upon penetration into the anatomical cavity, that movement of a safety member to the extended protruding position and/or retraction of a penetrating member, as well as automatic anchoring of the penetrating instrument, can be accomplished simultaneously and that the penetrating instrument of the present invention can be inexpensively manufactured with minimum components to reduce cost, facilitate sterilization for re-use and allow economical, single patient use.

The present invention is generally characterized in a penetrating instrument for penetrating an anatomical cavity wall to gain access to an anatomical cavity including a cannula having a distal end for being disposed in the anatomical cavity and a proximal end for being disposed externally of the anatomical cavity, a penetrating member disposed in the cannula and having a distal end for penetrating the anatomical cavity wall, a middle member disposed between the cannula and the penetrating member, the middle member having a distal end and a longitudinal axis, and a laterally-biased expandable portion disposed along the middle member a predetermined distance from the middle member distal end, the expandable portion being movable from an expanded position to a contracted position during penetration of the anatomical cavity wall and from the contracted position to the expanded position upon introduction of the expandable portion in the anatomical cavity. In the expanded position, the expandable portion has a configuration to anchor the cannula to protrude into the anatomical cavity a distance corresponding to the predetermined distance.

Another aspect of the present invention is generally characterized in a safety penetrating instrument for penetrating an anatomical cavity wall to gain access to an anatomical cavity including a penetrating member having a longitudinal axis and a distal end for penetrating the anatomical cavity wall, a safety member having a distal end and being movable relative to the penetrating member between and extended position where the safety member distal end protrudes distally from the penetrating member distal end and a retracted position where the safety member distal end is disposed proximally of the penetrating member distal end to expose the penetrating member distal end, extending means for moving the safety member distally to the extended position and for permitting the safety member to move proximally to the retracted position, handle means coupled with the safety member for manually moving the safety member proximally to the retracted position, locking means for locking the safety member in the retracted position during penetration of the anatomical cavity wall, an expandable portion carried by the safety penetrating instrument and being movable inwardly in a lateral direction transverse to the longitudinal axis from an expanded position to a contracted position during penetration of the anatomical cavity wall and outwardly in the lateral direction from the contracted position to the expanded position upon introduction of the expandable portion in the anatomical cavity, and releasing means responsive to movement of the expandable portion from the contracted position to the expanded position for triggering release of the locking means to permit the extending means to move the safety member to the extended position.

Yet another aspect of the present invention is generally characterized in a safety penetrating instrument for penetrating an anatomical cavity wall to gain access to an anatomical cavity including a cannula having a distal end for being disposed in the anatomical cavity and a proximal end for being disposed externally of the anatomical cavity, a penetrating member disposed within the cannula and having a distal end for penetrating the anatomical cavity wall, the penetrating member being movable relative to the cannula between an extended position where the distal end of the penetrating member protrudes distally from the distal end of the cannula and a retracted position proximally spaced from the extended position, retracting means for moving the penetrating member proximally from the extended position to the retracted position and for permitting the penetrating member to move distally to the extended position, handle means coupled with the penetrating member for manually moving the penetrating member distally to the extended position, locking means for locking the penetrating member in the extended position during penetration of the anatomical cavity wall, an expandable portion carried by the safety penetrating instrument and being movable inwardly in a lateral direction transverse to a longitudinal axis of the cannula from an expanded position to a contracted position during penetration of the anatomical cavity wall and outwardly in the lateral direction from the contracted position to the expanded position upon introduction of the expandable portion in the anatomical cavity, and releasing means responsive to movement of the expandable portion from the contracted position to the expanded position for triggering release of the locking means to permit the retracting means to move the penetrating member to the retracted position.

Still another aspect of the present invention is generally characterized in a safety penetrating instrument for penetrating an anatomical cavity wall to gain access to an anatomical cavity including a housing, a cannula having a proximal end mounted by the housing and a distal end for introduction in the anatomical cavity, the cannula being movable relative to the housing between an extended protruding position and a proximally spaced retracted position, a penetrating member disposed within the cannula and having a distal end for penetrating the anatomical cavity wall, the penetrating member being movable relative to the cannula between an extended position where the distal end of the penetrating member protrudes distally from the distal end of the retracted cannula and a retracted position where the distal end of the penetrating member is proximally spaced from the distal end of the extended cannula, extending means for moving the cannula distally to the extended position and for permitting the cannula to move proximally to the retracted position, retracting means for moving the penetrating member proximally to the retracted position and for permitting the penetrating member to move distally to the extended position, cannula locking means for locking the cannula in the retracted position during penetration of the anatomical cavity wall, penetrating member locking means for locking the penetrating member in the extended position during penetration of the anatomical cavity wall, an expandable portion carried by the safety penetrating instrument and movable inwardly in a lateral direction transverse to a longitudinal axis of the cannula from an expanded position to a contracted position during penetration of the anatomical cavity wall and outwardly in the lateral direction from the contracted position to the expanded position upon introduction of the expandable portion in the anatomical cavity, and releasing means responsive to movement of the expandable portion from the contracted position to the expanded position for triggering release of the locking means to permit the extending means to move the cannula to the extended position and the retracting means to move the penetrating member to the retracted position.

The above and still further objects, features and advantages of the present invention will become apparent from the following description of the preferred embodiments when considered in conjunction with the accompanying drawings wherein like reference numerals in the various figures are utilized to designate like components.

BRIEF DESCRIPTION OF THE DRAWINGS

FIG. 1 is a broken side view, partly in section, of a penetrating instrument according to the present invention.

FIG. 2 is a fragmentary perspective view of a distal end of the portal sleeve for the penetrating instrument of FIG. 1.

FIG. 3 is a fragmentary perspective view of a distal end of the middle member for the penetrating instrument of FIG. 1.

FIG. 4 is a perspective view of a membrane to be disposed over the expandable portion of the penetrating instrument of FIG. 1.

FIG. 5 is a fragmentary side view, in section, showing a modification of the expandable portion.

FIG. 6 is a fragmentary side view, partly in section, of the penetrating instrument of FIG. 1 during penetration of a wall of an anatomical cavity.

FIG. 7 is a fragmentary side view, partly in section, of the penetrating instrument of FIG. 1 following entry in the anatomical cavity.

FIG. 9 is a perspective view of a rail member for the penetrating instrument of FIG. 8.

FIG. 10 is a broken side view, partly in section, of the penetrating instrument of FIG. 8 during penetration of a wall of an anatomical cavity.

FIG. 11 is a broken side view, partly in section, of the penetrating instrument of FIG. 8 following entry in the anatomical cavity.

FIGS. 19–24 are fragmentary side views of modified penetrating members for the penetrating instrument of the present invention.

DESCRIPTION OF THE PREFERRED EMBODIMENTS

Figure 8:
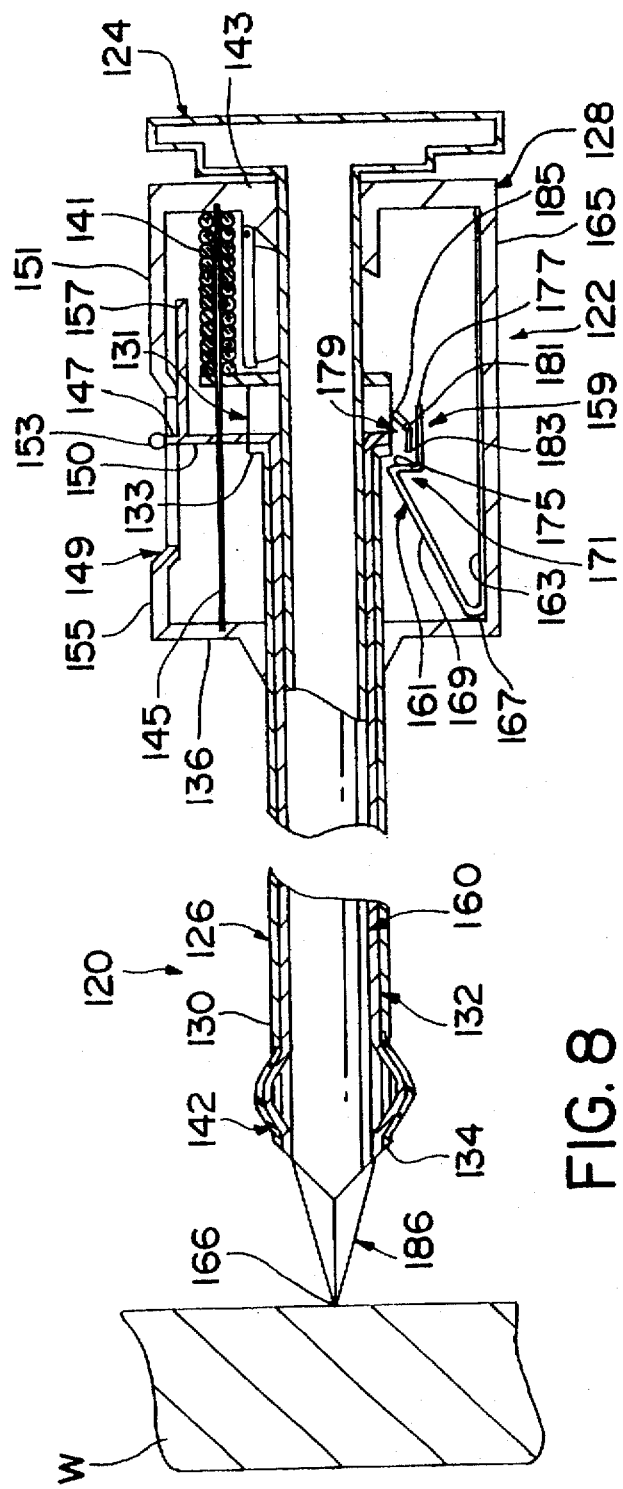
FIG. 8 is a broken side view, partly in section, of a modification of the penetrating instrument according to the present invention.

The safety penetrating instrument of the present invention is described hereinafter for use as an instrument for inserting a portal sleeve through a wall of an anatomical cavity to form a portal for the introduction of various surgical and diagnostic instruments into the cavity during endoscopic procedures, such as laparoscopy. It is understood, however, that the safety penetrating instrument of the present invention can be used for safe penetration or introduction into anatomical cavities of needles with fluid flow therethrough and catheters as well as for other instruments engaging tissue during surgical or diagnostic procedures. Accordingly, the cannula or outer tubular member of the safety penetrating instrument can be a portal sleeve, a needle, a catheter or a tubular component of a medical instrument.

A penetrating instrument 20 according to the present invention, as shown in FIG. 1, is formed of a portal unit 22 and a penetrating unit 24. The portal unit 22 includes an elongate portal sleeve, cannula or catheter 26, a middle member 32 disposed in portal sleeve 26 and a housing 28 mounting proximal ends of the portal sleeve and the middle member. Portal sleeve 26 defines a lumen for receiving a penetrating member of penetrating unit 24 and is made up of a body 30 terminating distally at a distal end 34 and proximally at a proximal end 38 secured to a front wall 36 of housing 28. Body 30 can be cylindrical, tubular or have any other desirable configuration in cross-section in accordance with the procedure to be performed and the anatomical cavity to be penetrated. As shown in FIG. 2, at least one longitudinally extending slot 40 and, preferably, a plurality of longitudinally extending slots 40 are formed in body 30. Slots 40 can be disposed adjacent the distal end 34 as shown or at any other desirable location along portal sleeve 26 in accordance with a desired amount of protrusion for the portal sleeve in an anatomical cavity as will be explained further below. As shown, slots 40 begin just inwardly or proximally of distal end 34 and extend in a proximal direction in alignment or parallel with a longitudinal axis of the penetrating instrument 20. The distance that the slots 40 extend longitudinally along the portal sleeve or, in other words, the length of slots 40, is dependent on the configuration of an expandable portion 42 of the instrument 20 in an expanded or anchoring position and the amount of longitudinal space or gap required between the portal sleeve and the expandable portion to permit movement of the expandable portion from the expanded position to a contracted position as will be explained further below. As shown in FIG. 1, slots 40 have a length to minimize any longitudinal gap or space between the expandable portion 42 in the expanded position and the body 30 while allowing movement of the expandable portion 42 to the contracted position. It will be appreciated that the number and spacing of slots 40 can vary in accordance with the number and spacing of strips or legs 44 of expandable portion 42 and that the width of slots 40 will be dependent on the width of the strips 44 as described more fully below. As shown in FIG. 2, the slots 40 are circumferentially spaced about the longitudinal axis to correspond with the spacing of strips 44.

Middle member 32, which carries expandable portion 42, terminates distally at a distal end 46 and proximally at a transverse flange 50 disposed in housing 28. Middle member 32 is disposed in portal sleeve 26, and the portal sleeve and the middle member are secured to one another distally of expandable portion 42. As shown in FIG. 1, the middle member distal end 46 is aligned or substantially aligned with the portal sleeve distal end 34, and the portal sleeve and the middle member are secured to one another at the distal ends 34 and 46. Middle member 32 can be cylindrical, tubular or have any other desired configuration in cross-section to be disposed between the portal sleeve and the penetrating member and to couple expandable portion 42 with flange 50. As shown, middle member 32 has a generally tubular configuration defining a lumen for receiving the penetrating member.

As shown in FIG. 3, expandable portion 42 includes one or more longitudinally extending legs or strips 44 corresponding in number and spacing to slots 40 and having opposing ends flexibly or pivotally connected to the middle member. The strips 44 are biased in a direction radially outwardly or transverse to the longitudinal axis to be normally disposed in the expanded position as shown in FIGS. 1 and 3. The portal sleeve 26 and the middle member 32 are arranged with slots 40 aligned with strips 44 to allow the strips 44 to extend, protrude or pass through the slots 40 in the expanded position as shown in FIG. 1. In the expanded position, strips 44 form an enlargement or protrusion along portal sleeve 26 having a configuration to anchor the instrument 20 relative to an anatomical cavity. As shown in FIG.

1, the enlargement formed by expandable portion 42 in the expanded position has a periphery, circumference or cross-section disposed outwardly of the periphery, circumference or cross-section of portal sleeve 26; and, preferably, the periphery, circumference or cross-section of portal sleeve 26 is disposed entirely within the periphery, circumference or cross-section of expandable portion 42 in the expanded position. Depending on the configuration of the strips 44, the enlargement can have a spherical, toroidal or doughnut shape, angular or any other desirable configuration. As shown, strips 44 have a somewhat convex curvature in the expanded position forming a rounded enlargement.

The outward bias for portion 42 can be selected to permit movement of the expandable portion inwardly toward the instrument longitudinal axis in the radial or transverse direction from the expanded position to the contracted position shown in FIG. 6 in response to resistance or force from anatomical tissue during penetration of an anatomical cavity wall and to permit movement of the expandable portion outwardly in the radial or transverse direction from the contracted position to the expanded position in response to a decrease, reduction or removal of the resistance or force upon penetration into the cavity. The bias for expandable portion 42 can also be selected to permit the expandable portion to be moved between the expanded and contracted positions manually such as with a handle coupled with the middle member and movable along a slot in the housing as shown in FIG. 8. In the contracted position, strips 44 are flattened or straightened to be disposed parallel or in alignment with or substantially parallel or in alignment with the longitudinal axis of the instrument such that the expandable portion 42 has an axial length in the contracted position greater than the axial length of the expandable portion 42 in the expanded position. Accordingly, movement of expandable portion 42 from the expanded to the contracted position causes middle member 32 and, therefore, flange 50, to move proximally relative to portal sleeve 26 as shown in dotted lines in FIG. 1, and movement of expandable portion 42 from the contracted position to the expanded position causes middle member 32 and flange 50 to move distally relative to portal sleeve 26. Additionally, in the contracted position, the periphery, circumference or cross-section of the expandable portion 42 is aligned or substantially aligned with the periphery, circumference or cross-section of portal sleeve 26 to facilitate passage of the portal sleeve through the anatomical tissue.

It should be appreciated that the middle member distal end need not be aligned with the portal sleeve distal end and that the middle member distal end can be disposed proximally or distally of the portal sleeve distal end. Accordingly, a distal end of the portal unit can be formed by the portal sleeve distal end, the middle member distal end or both the portal sleeve and the middle member distal ends where the distal ends are aligned. The middle member and the portal sleeve can be secured to one another at various locations in addition to their distal ends to cause the middle member to move proximally relative to the portal sleeve when the expandable portion is moved from the expanded to the contracted position.

The longitudinal distance from a distal end of the portal unit to a proximal end of the expandable portion 42 in the expanded position can be selected in accordance with the amount of protrusion into the anatomical cavity desired for the portal unit; and, therefore, the location of the expandable portion 42 along the instrument 20 can be selected in accordance with the amount of protrusion into the anatomical cavity desired for the portal unit. As shown in FIG. 1, the distance from the portal sleeve distal end 34 to a proximal end of expandable portion 42 in the expanded position is selected to obtain a predetermined amount of protrusion of the portal sleeve 26 into the anatomical cavity following penetration. Accordingly, the expandable portion 42 can be provided along the penetrating instrument at various distances from the portal unit distal end, as shown in dotted lines in FIG. 1, in accordance with the amount of protrusion into the anatomical cavity desired for the portal unit; and the expandable portion can be located to obtain various predetermined amounts of protrusion for various procedures. It will be appreciated, therefore, that expandable portion 42 is illustrated herein adjacent a distal end of the portal sleeve by way of example only.

The outward bias for expandable portion 42 can be provided in many various ways such as by forming strips 44 of a resilient spring material or a material having shape memory, such that the outward bias is provided by the strips themselves, or by utilizing a separate bias device, such as a spring 45, disposed between flange 50 and a rear wall of housing 28.

FIG. 4 illustrates a stretchable, flexible, deformable, resilient or elastic membrane or sheath 54 to be disposed over expandable portion 42. Membrane 54 can have a tubular or cylindrical cross-section as shown or any other desired configuration in cross-section to cover expandable portion 42 in the expanded and contracted positions. Membrane 54 can be disposed between the middle member 32 and the portal sleeve 26 to cover expandable portion 42 as shown, or the membrane Can be disposed over the portal sleeve 26. The membrane 54 can be secured, such as with adhesive, to the middle member and/or the portal sleeve or the membrane can be made to fit snugly or tightly over the middle member or the portal sleeve. The membrane 54 can be made of any suitable stretchable, flexible, resilient, deformable or elastic medical grade material, such as silicone rubber or sponge, to conform or stretch to the configuration and size of the expandable portion 42 in the expanded position. Where the membrane 54 is disposed between the portal sleeve and the middle member, the membrane will be moved through slots 40 by the strips 44 in the expanded position. The membrane 54 can have a length to cover portion 42 and can extend to the distal end of the portal unit.

Referring again to FIG. 1, the housing 28 is preferably constructed to sealingly engage instruments passing therethrough and to include a valve 56 biased to a closed state when no instrument passes through the portal sleeve. Valve 56 is shown as a flapper valve; however, any suitable valve construction can be utilized including, for example, trumpet or nipple valves. Housing 28 can have any desirable configuration in cross-section to facilitate grasping by the surgeon and includes transverse internal walls 58 extending from upper and lower walls of the housing to serve as a stop or abutment limiting proximal movement of flange 50 when expandable portion 42 is moved to the contracted position.

The penetrating unit 24 includes an elongate penetrating member 60 for being received in the lumen of portal sleeve 26 and having a proximal end mounted by a hub 64, a distal end 86 having a sharp tip or point 66 and a shaft or body extending between the proximal and distal ends. The distal end can have any configuration desired by a surgeon for a particular procedure, for example, the pyramidal trocar configuration shown or conical, threaded, multifaceted or open, slanted or needle configurations. The penetrating member 60 can be made of any suitable, medical grade materials and can be made of multiple components such that, for example, the distal tip can be made of stainless steel and secured in any conventional manner, such as by threads, to the distal end of the shaft, which can be tubular and made of a less expensive material, such as plastic or metal. The hub 64 can have any desired external configuration to facilitate grasping of the portal unit and the penetrating unit by the surgeon with one hand.

The portal unit 22 and the penetrating unit 24 can be provided to a surgeon separately or assembled together as shown in FIG. 1, and either or both of the portal and penetrating units can be manufactured in a manner to be disposable for single patient use or to be sterilizable for re-use. The hub 64 can be coupled to the housing 28 by suitable detent or latch mechanisms if desired, and the penetrating unit 24 can be withdrawn from the portal unit 22 leaving the portal sleeve 26 in place within an anatomical cavity.

FIG. 5 illustrates a modification 42' of the expandable portion wherein strips 44', instead of being curved in the expanded position, are formed of straight segments 44a' and 44b' flexibly or pivotally connected at joints, pivots or hinges 44c'. The expandable portion 42' is biased to the expanded position where the straight segments 44a' and 44b' are pivoted relative to one another along the pivots 44c' to form an angular configuration. The segments 44a' and 44b' and the pivots 44c' can be made as separate components or can be of integral one-piece construction. In the expanded position for portion 42', the pivots 44c' are disposed outwardly of the periphery of body 30 of the portal sleeve with segment 44a' angled proximally and segment 44b' angled distally. In the contracted position, the segments 44a' and 44b' will be longitudinally axially aligned or substantially longitudinally axially aligned parallel or in alignment with or substantially parallel or in alignment with the longitudinal axis of the instrument.

In use, when a surgeon desires to penetrate into an anatomical cavity using the penetrating instrument 20, the instrument is in the condition shown in FIG. 1 with the penetrating member 60 extending from the distal end of the portal sleeve 26 and the expandable portion 42 in the expanded position with flange 50 biased into abutment with the housing forward wall. When the sharp distal end 66 of the penetrating member is brought into contact with tissue forming an anatomical cavity wall W, the force-to-penetrate is limited to the force required to cause sharp distal end 66 to pass through the cavity wall W, and the portal sleeve and the penetrating member do not move longitudinally during penetration. As penetration continues, a force from the anatomical tissue surrounding the portal sleeve 26 will compress, collapse or contract expandable portion 42 inwardly causing movement of portion 42 from the expanded position to the contracted position as shown in FIG. 6 to facilitate movement of portal sleeve 26 through the anatomical cavity wall. Movement of expandable portion 42 from the expanded position to the contracted position causes longitudinal proximal movement of middle member 32 relative to portal sleeve 26 until flange 50 abuts internal walls 58 which serve as a stop limiting proximal movement of the middle member. Once the expandable portion 42 has passed through the anatomical cavity wall W, the force from tissue contact will be reduced, decreased or removed causing expandable portion 42 to move from the contracted position to the expanded position due to the bias of strips 44 as shown in FIG. 7 to anchor the instrument 20 relative to the anatomical cavity wall. Movement of expandable portion 42 from the contracted position to the expanded position causes longitudinal distal movement of middle member 32 relative to portal sleeve 26 such that flange 50 is again in abutment with the housing front wall. With the expandable portion in the expanded position, the portal sleeve 26 will be anchored in the anatomical cavity and will protrude from the cavity wall into the anatomical cavity a predetermined distance corresponding to the position of the expandable portion. The penetrating unit 24 can be withdrawn from the portal unit 22 leaving the portal sleeve in place such that instruments for performing endoscopic procedures can be introduced into the cavity via the portal formed by the portal unit.

Many various procedures can be conducted via the portal sleeve 26 with greater security in that the expandable portion 42 prevents inadvertent backing out of the portal sleeve from the anatomical cavity wall. Upon completion of the procedures, the portal sleeve can be withdrawn from the anatomical cavity with a manual force sufficient to cause the portion 42 to be moved to the contracted position, and removal of the portal sleeve can be facilitated by providing a proximal end of the portion 42 with a distal angle or slope as shown. Furthermore, a handle can be coupled with the middle member and utilized to move the middle member proximally such that the expandable portion is moved from the expanded position to the contracted position in order to facilitate removal of the portal sleeve from the anatomical cavity.

It will be appreciated that the expandable portion can be designed in many various ways in addition to the strips shown herein; for example, the expandable portion can include various springs, including coil springs, as well as inflatable membranes, and the expandable portion can be used with or without the protective membrane or sheath. It will further be appreciated that the expandable portion can be designed to be moved manually between the expanded and contracted positions during use rather than or in addition to be moved automatically in response to a force from anatomical tissue. The handle and slot structure disclosed herein below can be utilized to manually expand and contract the expandable portion; however, various other means can be utilized to manually expand and contract the expandable portion. Where the penetrating instrument is provided with means for manually moving the expandable portion, such means can be utilized to move the expandable portion to the contracted position to facilitate withdrawal of the penetrating instrument fro the anatomical cavity.

A modification of the penetrating instrument according to the present invention is shown in FIG. 8 at 120 and includes a portal unit 122 and a penetrating unit 124, the penetrating unit 124 being similar to the penetrating unit 24. Portal unit 122 is similar to portal unit 22 and includes portal sleeve 126, middle member 132 and housing 128. Portal sleeve 126, which serves as a safety member, is similar to portal sleeve 26 except that body 130 of portal sleeve 126 terminates proximally at a U-shaped rail member 131 disposed in housing 128. As shown in FIG. 9, rail member 131 includes a forward wall 133 disposed transverse or perpendicular to a longitudinal axis of the penetrating instrument 120 and parallel or substantially parallel to flange 150, a rearward wall 135 spaced from and parallel to forward wall 133 and a side wall 137 transversely joining the forward and rearward walls. Rearward wall 135 extends toward an upper wall 151 of housing 128, and an extending member 141 is mounted between the rail member rearward wall 135 and a rear wall 143 of housing 128 to bias the portal sleeve 126 in a distal direction to an extended protruding position where distal end 134 of the portal sleeve is disposed beyond the sharp tip 166 of the penetrating member 160 as explained further below. The extending member 141 can include a helical coil spring mounted in compression between rail member rearward wall 135 and the housing rear wall 143 as shown or any other type of spring or other bias device including tension springs, compression springs, torsion springs, pan springs, pivotally connected members, rubber, plastic or magnets, for example. If desired, a guide rod can be connected between a front wall 147 and the rear wall 143 of housing 128 with the spring 141 disposed around the guide rod.

Middle member 132 is similar to middle member 32 and terminates proximally at a transverse flange 150 disposed between the forward and rearward walls of rail member 131. Middle member 132 can have any configuration in cross-section to connect or couple operating flange 150 with expandable portion 142 including cylindrical, tubular or partly tubular configurations. A pin 147 extends from flange 150 through a slot 149 in an upper wall 151 of the housing to terminate at a handle or knob 153 positioned in an elongate, trough-like recess 155 in the upper wall. Slot 149 and recess 155 extend longitudinally in parallel with the longitudinal axis of the penetrating instrument 120. An indicator strip 157 extends perpendicularly from flange 150 towards the proximal end of the instrument to be visible through and along the length of slot 149 when the portal sleeve is in the extended position as will be described further below. The indicator strip 157 can be colored and/or can be provided with any suitable indicia, and the slot 149 or the recess 155 can be provided with a transparent window or cover for viewing of the indicator strip therethrough. The expandable portion 142 is similar to expandable portion 42 and is biased to the expanded position wherein flange 150 is in abutment with the forward wall 133 of the rail member with the penetrating member 160 passing through the rail member 131.

Housing 128 is similar to housing 28 and mounts a locking and releasing mechanism 159 for locking the portal sleeve 126 in a retracted position exposing the sharp distal tip 166 of the penetrating member 160 and for releasing the portal sleeve to allow the portal sleeve to move to the extended protruding position. Locking and releasing mechanism 159 includes a latch or locking spring 161, made of a strip of resilient material, formed to have a substantially flat base 163 secured to a lower wall 165 of housing 128 or to a structure within the housing and a bend 167 joining the base 163 with an upwardly angled arm 169 spaced from the base. Arm 169 carries or forms a latch 171 having a distal angled latching surface joining a proximal angled latching surface 175 disposed substantially transverse to the longitudinal axis of the penetrating instrument and substantially parallel to the rail member forward wall 133. Arm 169 has an extension 177 extending perpendicularly from latch 171 in a proximal direction, and a releasing or trigger member 179 is juxtaposed with extension 177. The trigger 179 is pivotally mounted in the housing on a pin 181 secured to a wall or walls of the housing or a structure supported in the housing, and the trigger is generally L-shaped with a leg 183 overlying extension 177 and a leg 185 extending substantially transversely from leg 183 but at a slight angle toward the proximal end of the safety penetrating instrument. A torsion spring (not shown) is coiled around pin 181 and fixed to trigger 179 to bias the trigger counterclockwise looking at FIG. 8 such that leg 183 is biased toward extension 177.

In use, the safety penetrating instrument 120 will normally be provided in the condition illustrated in FIG. 11 with the expandable portion 142 in the expanded position and the portal sleeve 126 in the extended position to cover the sharp distal tip 166 of the penetrating member 160. With the safety penetrating instrument 120 in the condition shown in FIG. 11, flange 150 will be in abutment with the forward wall 133 of rail member 131 due to the bias of portion 142, and handle 153 will be disposed at a distal end of slot 149 with indicator strip 157 viewable along the length of the slot 149 due to the bias of extending member 141. Prior to commencing penetration of an anatomical wall W, handle 153 is grasped and manually moved proximally to move portal sleeve 126 proximally against the bias of extending member 141 until rail member forward wall 133 rides over latch 171 by engaging the distal latching surface to move arm 169 toward base 163. At this time, the surgeon can feel the rail member lock into place with the rail member forward wall 133 in engagement with proximal latching surface 175 as arm 169 springs back and can also visually determine that the portal sleeve is locked in the retracted position by noting the position of handle 153 at a proximal end of slot 149 at which time the indicator strip 157 will no longer be visible or will be only slightly visible.

The penetrating instrument 120 is now in the position illustrated in FIG. 8 with the portal sleeve 126 locked in the retracted position by locking and releasing mechanism 159 and the penetrating member 160 extending from the distal end of the portal sleeve. With the portal sleeve 126 locked in the retracted position, the expandable portion 142 will be in the expanded position with flange 150 in abutment with the forward wall 133 of rail member 131 and disposed distally of leg 185 of trigger 179.

As penetration of the anatomical cavity wall W is commenced, the force-to-penetrate is limited to the force required to cause sharp distal end 166 to pass through the cavity wall W since neither the penetrating member nor the portal sleeve moves longitudinally during penetration. As penetration continues, the penetrating instrument will advance through the cavity wall W as shown in FIG. 10, and expandable portion 142 will be moved to the contracted position facilitating passage of the portal sleeve through the anatomical cavity wall. Movement of expandable portion 142 from the expanded to the contracted position during penetration of the anatomical cavity wall W causes the operating member formed by flange 150 to move proximally until flange 150 abuts the rearward wall 135 of rail member 131 which serves as a stop or abutment limiting proximal movement of the operating member. As the flange 150 moves proximally, the operating member formed thereby engages leg 185 to pivot trigger 179 clockwise, looking at FIG. 10, to allow the operating member to pass thereby. The clockwise pivotal movement of trigger 179 does not cause movement of the latch 171 since there is no engagement by either leg 183 or 185 with arm extension 177. Accordingly, the force-to-penetrate is limited to the force required to cause the sharp distal end 166 to pass through the cavity wall W since no force is required to overcome the bias of extending member 141.

Once the expandable portion 142 has entered the anatomical cavity, the expandable portion 142 will be returned to the expanded position causing the flange 150 to move distally. As the flange 150 moves distally, the operating member formed thereby engages leg 185 of trigger 179 causing the trigger to pivot counterclockwise looking at FIG. 10 and causing leg 183 to engage arm extension 177 moving arm 169 toward base 163 against the force of spring strip 161. The movement of arm 169 away from the longitudinal axis of the safety penetrating instrument causes latch 171 to move out of engagement with rail member forward wall 133 thereby allowing extending member 141 to move the portal sleeve distally to the extended protruding position where distal end 134 protrudes beyond the sharp distal tip 166 of the penetrating member as illustrated in FIG. 11. Once portion 142 has moved from the contracted position to the expanded position upon penetration into the anatomical cavity, the instrument can be pulled back toward the cavity wall until the enlargement formed by portion 142 is adjacent or in abutment with an internal surface of the cavity wall at which time the portal sleeve will be anchored relative to the anatomical cavity wall to prevent backing out of the portal sleeve from the anatomical cavity. The portal sleeve will be anchored to protrude into the anatomical cavity a distance corresponding to the distance from the portal sleeve distal end to a proximal end of expandable portion 142.

Although the portal sleeve is disclosed herein as the safety member, it will be appreciated that the safety member can be any other member including a shield or probe. By forming extending member 141 to be relatively strong, protrusion of the safety member is assured even should the safety member engage tissue in the anatomical cavity wall or within the anatomical cavity or should any tissue be jammed between the safety member and the penetrating member. Additionally, the strong force of extending member 141 provides the surgeon with the psychological benefit of knowing the safety member is protecting the penetrating member. Should tissue within the anatomical cavity be contacted by the distal end of the safety member, the safety member can bounce or give a little in the manner of a shock absorber to protect such contacted tissue. Additionally, movement of the safety member can be seen by the surgeon by noticing movement of handle 153 toward a distal end of slot 149 and observation of indicator strip 157. The strong force of extending member 141 also provides the surgeon with an easily felt tactile signal that the safety member has moved to the extended position and that penetration into the cavity has occurred which also can be visually confirmed by the position of handle 153 and indicator strip 157. The outward bias of portion 142 need only be strong enough to produce a slight longitudinal movement of flange 150 past the trigger such that the force-to-penetrate is minimized.

Release of the safety member to move distally to the extended protruding position can be triggered by movement of an operating member connected with the expandable distal portion, and the expandable distal portion can be carried on the safety member as shown or on the penetrating member or on any other member to trigger release of the safety member. As described above, the operating member is carried by the safety member to limit the number of components in the safety penetrating instrument; however, the operating member could be carried on any member coupled to the expandable portion to transmit longitudinal movement to the operating member. The safety member can have various configurations so long as the distal end protrudes beyond the sharp tip of the penetrating member to provide a protective function, and a plurality of safety members can be employed in the penetrating instrument.

Figure 12:
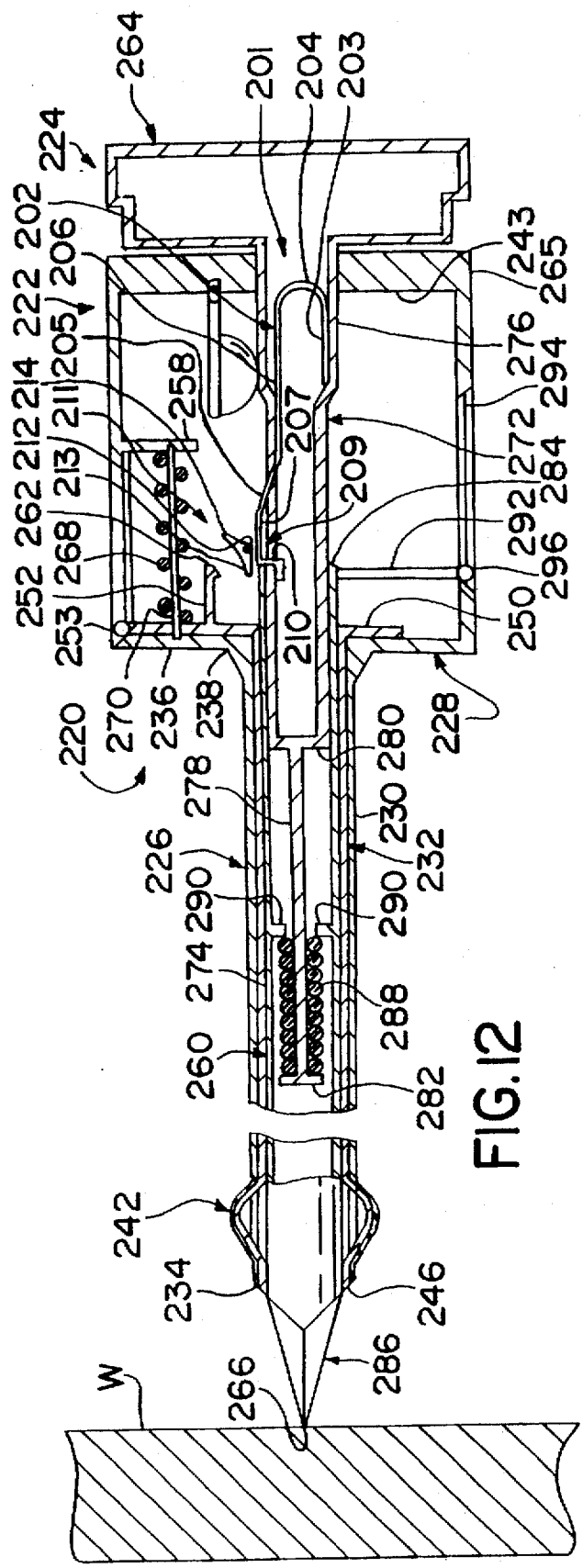
FIG. 12 is a broken side view, partly in section, of another modification of the penetrating instrument according to the present invention.

Another modification of the safety penetrating instrument according to the present invention is illustrated in FIG. 12 at 220 and is formed of a portal unit 222 and a penetrating unit 224. Portal unit 222 is similar to portal units 22 and 122 and includes an elongate portal sleeve, cannula or catheter 226, a middle member 232 with an expandable portion 242 and a housing 228 mounting proximal ends of the portal sleeve in the middle member. Penetrating unit 224 is similar to penetrating units 24 and 124 and includes an elongate penetrating member 260 disposed in portal sleeve 226 and a hub 264 mounting a proximal end of the penetrating member. Hub 264 can be latched to housing 228 with the use of any suitable releasable mechanism, such as detents operated by buttons, allowing the hub to be removed from the housing withdrawing the penetrating member from the portal sleeve.

Housing 228 is similar to housing 28 and includes front and rear walls 236 and 243 having aligned openings therein to allow passage therethrough by the penetrating member 260. Portal sleeve 226 is similar to portal sleeve 26 and includes a proximal end 238 secured to the housing front wall 236.

Middle member 232, which carries expandable portion 242, terminates distally at a distal end 246 and proximally at a transverse flange 250 disposed in housing 228 with the middle member passing through an opening in the housing front wall 236. Flange 250 is disposed transverse or perpendicular to the instrument longitudinal axis, and a finger 252 extends perpendicularly from flange 250 in a proximal direction to terminate at a barb 262 that is angled distally from finger 252 in the direction of the instrument longitudinal axis.

A bias device for biasing the strips 244 of the expandable portion 242 to the expanded position is illustrated in FIG. 12 and includes a spring or other bias member 268 mounted between flange 250 and a transverse inner wall or shoulder 258 depending from the upper wall of housing 228. If desired, a guide rod 270 can be connected between the housing front wall 236 and the shoulder 258 with the spring 268 mounted on the guide rod. Spring 268 biases middle member 232 distally to cause flange 250 to abut housing forward wall 236 and strips 244 to protrude through slots 240 to be disposed in the expanded position. It should be appreciated, however, that where the outward bias is provided by the strips themselves, flange 250 can be biased by expandable portion 242 to abut housing forward wall 236 without the need for bias member 268. Bias member 268 can be designed in many various ways to include, for example, tension springs, compression springs, torsion springs, pan springs, rubber, plastic or magnets.

Penetrating member 260 is made up of an inner or end part 272 and an outer or distal part 274 mounted for telescoping, sliding movement relative to end part 272. End part 272 includes a tubular or hollow or partly tubular or hollow rearward section 276 and a forward section 278 having a periphery, circumference or cross-section smaller than a periphery, circumference or cross-section of rearward section 276. Rearward section 276 terminates proximally at the proximal end of the penetrating member secured to hub 264 and distally at a transverse stop or end wall 280. Forward section 278 extends distally from end wall 280 to terminate at a transverse flange 282 disposed in distal part 274. Distal part 274 is hollow or tubular or partly hollow or tubular to receive forward section 278 and has an inner diameter or size to closely receive a portion of rearward section 276. Distal part 274 terminates proximally at an edge or shoulder 284 disposed in housing 228 and distally at a distal end 286 having a sharp tip or point 266 for penetrating anatomical tissue. The distal end 286 can have any configuration desired by a surgeon for a particular procedure, for example, the pyramidal trocar configuration shown or conical, threaded, multi-faceted or open, slanted or hollow or tubular needle configurations. The penetrating member 260 can be made of any suitable, medical grade materials and can be made of multiple components such that, for example, the distal end 286 can be made of stainless steel and secured in a conventional manner, such as by threads, to a shaft or body of the penetrating member, which can be tubular and made of a less expensive material, such as plastic or metal.

A retracting member 288 biases distal part 274 proximally relative to end part 272 and includes a helical coil spring disposed around the forward section 278 and mounted between flange 282 and an internal transverse shoulder 290 of distal part 274 to bias the penetrating member to a retracted position where the sharp tip 266 is protected and not exposed. The penetrating member can be biased to the retracted position in many various ways in addition to spring 288 and can include, for example, tension springs, compression springs, torsion springs, pan springs, rubber, plastic or magnets.

A plate, flange or rod 292 extends from distal part 274 to extend through a longitudinal slot 294 in a lower wall 265 of housing 228 and terminates at a knob or handle 296. If desired, the housing lower wall can be formed with a trough or recess with slot 294 positioned in the recess.

A locking and releasing mechanism 201 for locking the penetrating member 260 in an extended position where the sharp tip 266 is exposed and for releasing the penetrating member to move to the retracted position includes a latch or locking spring 202 disposed in rearward section 276 and made of a strip of resilient material formed to have a substantially flat base 203 secured to a wall of rearward section 276 or to structure in rearward section 276 and a bend 204 joining base 203 with an arm 205 spaced from the base. Arm 205 has a segment 206 extending distally from bend 204 parallel or substantially parallel with base 203 and an extension 207 extending angularly outwardly from segment 206 to extend or protrude through a slot 208 in rearward section 276. Arm 205 carries or forms a latch 209 having a distal angled latching surface 210 extending inwardly from extension 207 to be disposed substantially transverse to the longitudinal axis of the retractable safety penetrating instrument. A releasing or trigger member 211 is juxtaposed with extension 207 and is pivotally mounted in the housing 228 on a pin 212 secured to a wall or walls of the housing or structure supported in the housing. The trigger 211 includes a leg 213 overlying extension 207 and a leg 214 extending substantially transverse from leg 213 but at a slight angle toward the proximal end of the retractable safety penetrating instrument. A torsion spring (not shown) is coiled around pin 212 and fixed trigger 211 to bias the trigger counterclockwise looking at FIG. 12 such that leg 213 is biased toward extension 207. Trigger 211 is arranged in housing 228 with leg 214 disposed in the path of longitudinal movement of barb 262 when flange 250 is moved in response to movement of expandable portion 242 between the expanded and contracted positions.

Figure 14:
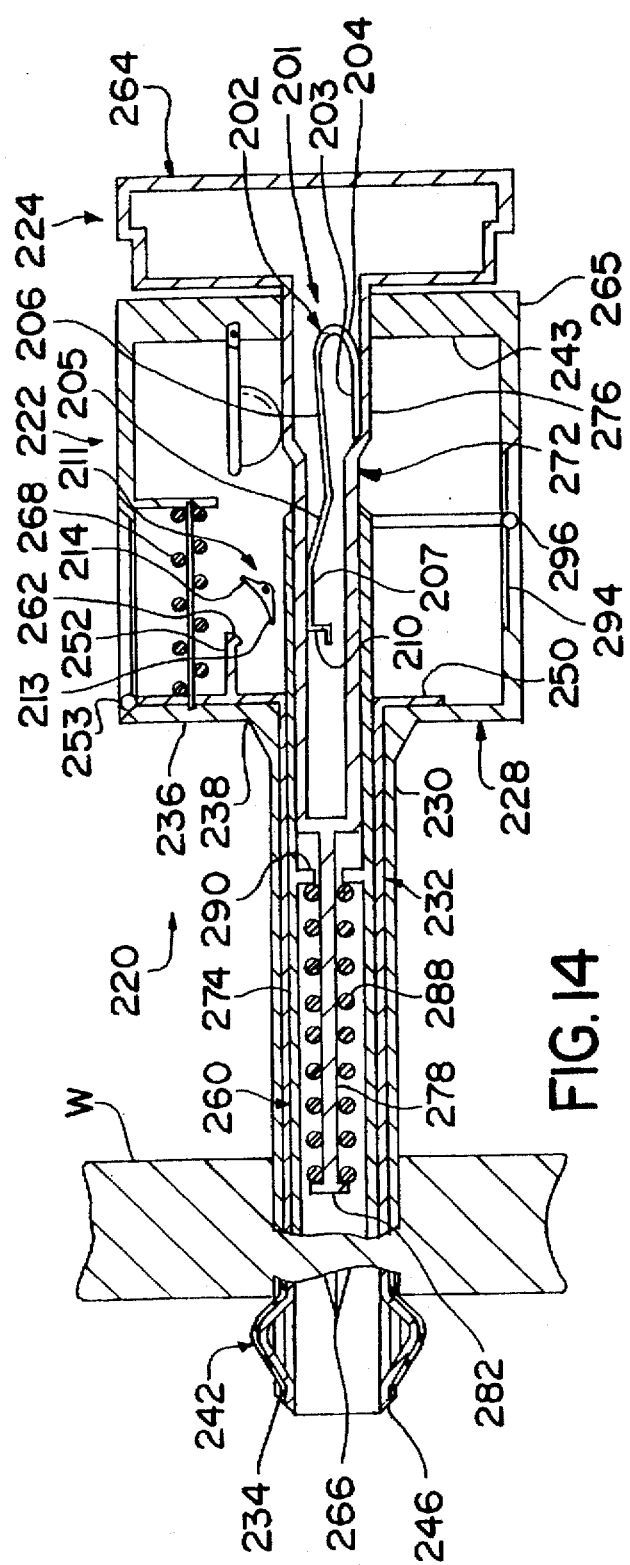
FIG. 14 is a broken side view, partly in section, of the penetrating instrument of FIG. 12 following entry in the anatomical cavity.

In use, the retractable safety penetrating instrument 220 can be provided in the condition illustrated in FIG. 14 with expandable portion 242 in the expanded position and penetrating member 260 in the retracted position where sharp tip 266 is disposed proximally of the distal end of the portal unit to be in a safe protective position. With the retractable safety penetrating instrument in the condition illustrated in FIG. 14, flange 250 will be biased to abut housing front wall 236 and handle 296 will be disposed toward a proximal end of slot 294. Prior to commencing penetration of an anatomical cavity wall W, handle 296 is grasped and manually moved distally to move penetrating member distal part 274 distally against the bias of spring 288 until edge 284 moves past latch 209 causing arm 205 to spring back to its normal position of FIG. 12.

The retractable safety penetrating instrument is now in the position illustrated in FIG. 12 with the penetrating member 260 locked in the extended position by locking and releasing mechanism 201 and the sharp tip 266 of the penetrating member disposed beyond the distal end of the portal unit. At this time, edge 284 will be in engagement with latching surface 210 and handle 296 will be disposed a distal end of slot 294. The expandable portion 242 will remain in the expanded position with flange 250 in abutment with housing front wall 236 and barb 262 disposed distally of trigger leg 214.

Figure 13:
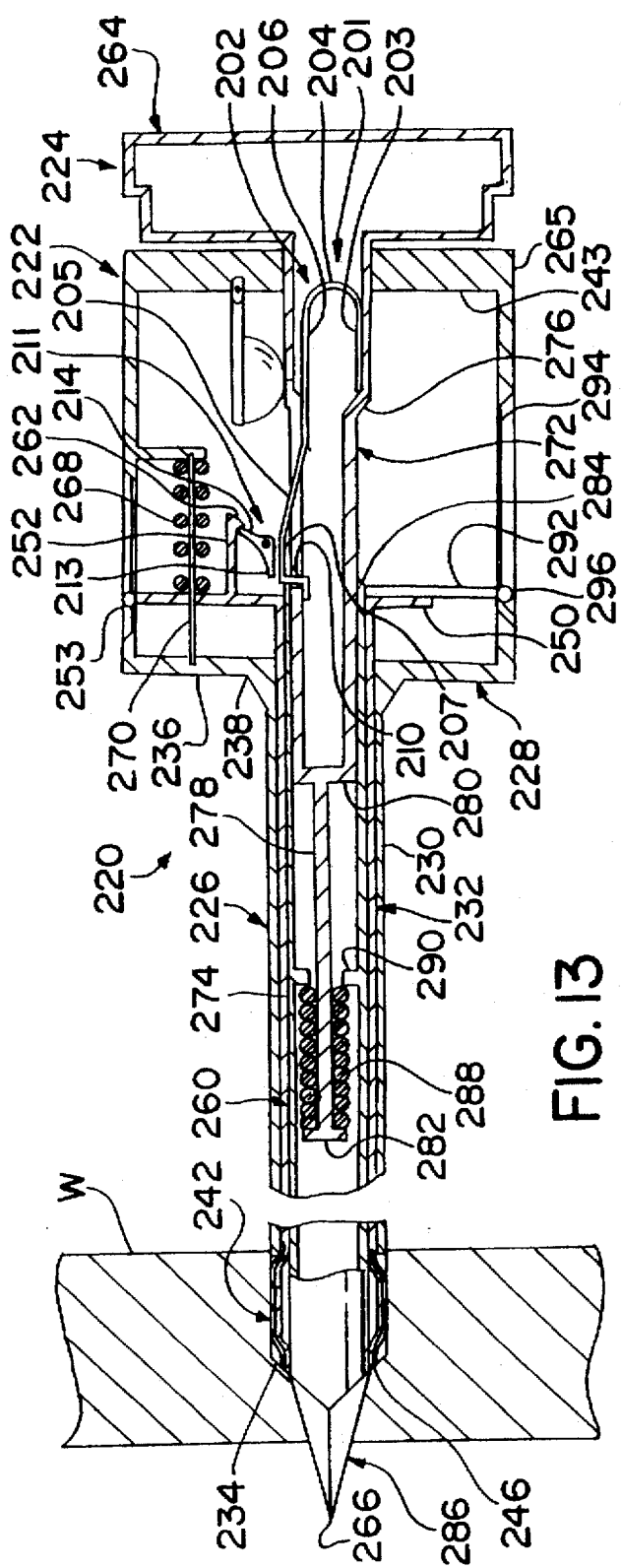
FIG. 13 is a broken side view, partly in section, of the penetrating instrument of FIG. 12 during penetration of a wall of an anatomical cavity.

As penetration of the anatomical cavity wall W is commenced, the force-to-penetrate is limited to the force required to cause sharp distal end 286 to pass through the cavity wall W since neither the penetrating member nor the portal sleeve moves longitudinally during penetration. As penetration continues, the retractable safety penetrating instrument will advance through the cavity wall W as shown in FIG. 13, and the expandable portion 242 will be moved to the contracted position automatically due to the force from resistance of the anatomical tissue or manually via handle 253. In the contracted position, expandable portion 242 is collapsed thusly facilitating passage of the portal sleeve through the anatomical cavity wall. Movement of expandable portion 242 from the expanded to the contracted position during penetration of the anatomical cavity wall W causes the operating member formed by flange 250 and barb 262 to move proximally until flange 250 abuts the plate 292 which serves as a stop or abutment limiting proximal movement of the middle member. As the flange 250 moves proximally, barb 262 moves proximally past trigger leg 214 without causing movement of latch 209 since there is no engagement by either leg 213 or 214 with arm extension 207.

Once the expandable portion 242 has entered the anatomical cavity the expandable portion will be returned to the expanded position automatically due to a reduction in the force from tissue contact or manually via handle 253 causing the operating member formed by flange 250 and barb 262 to move distally. As the flange 250 moves distally, barb 262 engages trigger leg 214 causing the trigger to pivot or rotate counterclockwise looking at FIG. 13 and causing leg 213 to engage arm extension 207 moving arm 205 toward base 203 against the force of spring strip 202. The movement of arm 205 in the direction of the longitudinal axis of the retractable safety penetrating instrument causes latch 209 to move out of engagement with end 284 thereby allowing retracting spring 288 to move the distal part 274 of the penetrating member in a proximal direction relative to the end part 272 to the retracted position illustrated in FIG. 14 wherein the sharp distal tip 266 is disposed within the portal sleeve. Shoulder 290 can be arranged to abut end wall 280 in the retracted position such that end wall 280 serves as a stop or abutment limiting proximal movement of distal part 274. In addition to triggering retraction of the penetrating member 260, movement of expandable portion 242 from the contracted position to the expanded position upon penetration into the anatomical cavity simultaneously anchors the portal sleeve 226 relative to the anatomical cavity wall W to prevent backing out of the portal sleeve from the anatomical cavity, and the portal sleeve will be anchored to protrude a predetermined distance into the anatomical cavity. With the portal unit anchored relative to the anatomical cavity, the penetrating unit can be withdrawn from the portal unit leaving the portal sleeve in place such that instruments for performing endoscopic procedures can be introduced into the cavity via the portal formed by the portal unit.

Figure 15:
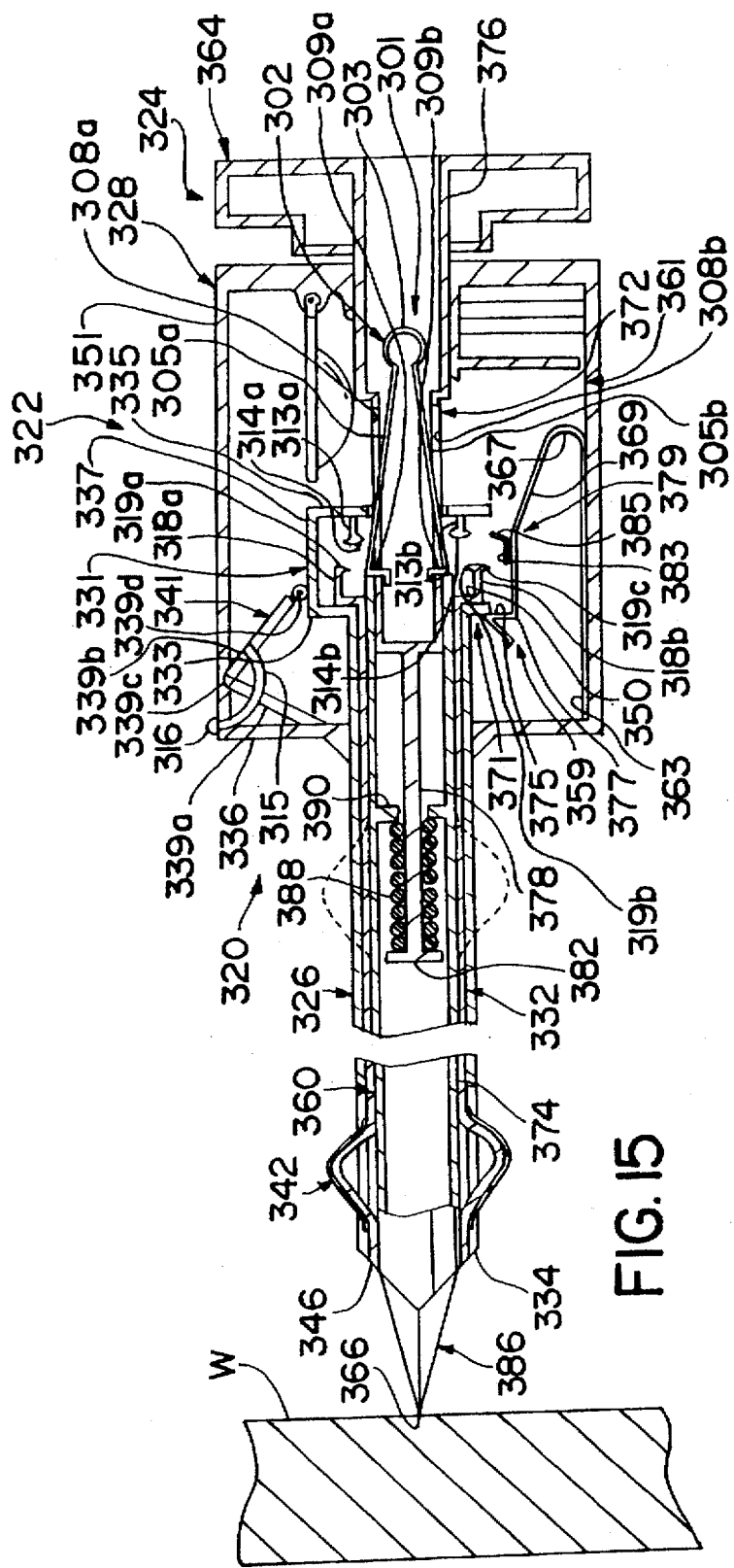
FIG. 15 is a broken side view, partly in section, of yet another modification of the penetrating instrument according to the present invention.

A further modification of the safety penetrating instrument according to the present invention is illustrated in FIG. 15 at 320. Safety penetrating instrument 320 is similar to safety penetrating instrument 220 in that expandable portion 342 for safety penetrating instrument 320 triggers retraction of penetrating member 360; however, expandable portion 342 also triggers protrusion of portal sleeve 326 to serve as a safety member for the safety penetrating instrument 320. Safety penetrating instrument 320 includes a portal unit 322 made up of portal sleeve 326, middle member 332 and housing 328. Portal sleeve 326 is similar to portal sleeve 226 for safety penetrating instrument 220 except that portal sleeve 326 terminates proximally at a rail member 331 disposed in housing 328 with the portal sleeve passing through an opening in the housing front wall 336. Rail member 331 is generally U-shaped and includes a forward wall 333 disposed transverse or perpendicular to a longitudinal axis of the safety penetrating instrument, a rearward wall 335 parallel to forward wall 331 and a side wall 337 joining the rail member forward and rearward walls. An extending member 341 is connected between the housing front wall 336 and the rail member 331 to bias the rail member and, therefore, the portal sleeve 326, distally to a portal sleeve or safety member extended position. Extending member 341 can include various tension springs, compression springs, pan springs, torsion springs, rubber, plastic or magnets, for example, or any other bias device. As shown in FIG. 15, the extending member 341 is made up of legs 339a and 339b flexibly or pivotally connected to one another at a flexible joint, pivot or hinge 339c. Leg 339a is connected between housing forward wall 336 and pivot 339c, which is disposed along an upper wall of the housing, and leg 339b is connected between pivot 339c and a flexible joint, pivot or hinge 339d along rail member 331, the pivot 339d being disposed along the rail member side wall 337. A torsion spring (not shown) can be disposed around pivot 339c and connected between housing 328 and leg 339b to bias leg 339b distally toward leg 339a to bias the portal sleeve to the portal sleeve extended position. A curved segment 315 extends from leg 339b through a slot or opening in an upper wall 351 of housing 328 to terminate at a knob, button or handle 316 with the curve segment being movable in and out of the housing. Middle member 332 carries expandable portion 342 and is similar to middle member 232. Middle member 332 terminates proximally at flange 350 disposed between forward and rearward walls 333 and 335 of the rail member. Fingers 318a and 318b extend perpendicularly transversely from flange 350 in a proximal direction from opposite sides of the instrument longitudinal axis. One of the fingers 318a terminates at a barb 319a that is angled distally from the one finger 318a in the direction of the instrument longitudinal axis. The other of the fingers 318b terminates at a prong having a hook-like configuration with a barb 319b curving distally from finger 318b in the direction of the instrument longitudinal axis and an opposing barb 319c curving distally from finger 318b in a direction away from the instrument longitudinal axis.

Penetrating member 360 for safety penetrating instrument 320 is similar to penetrating member 260 and includes an end part 372 and a distal part 374 mounted for telescoping sliding movement relative to end part 372. A locking and releasing mechanism 301 for locking the penetrating member 360 in the penetrating member extended position and for releasing the penetrating member to move to the penetrating member retracted position includes a latch or locking spring disposed in rearward section 376 of end part 372 and made of a strip of resilient material formed to have a partial or semi-circular base 303 supported by a wall of rearward section 376 or by structure in the rearward section and a pair of arms 305a and 305b angled outwardly from opposing ends of base 303 in a direction away from the instrument longitudinal axis to extend distally to protrude through opposing slots 308a and 308b in the rearward section. Arms 305a and 305b carry a form latches 309a and 309b having distal angled latching surfaces extending inwardly from arms 305a and 305b, respectively, in the direction of the longitudinal axis to be disposed substantially transverse to the longitudinal axis. Releasing or trigger members are juxtaposed with arms 305a and 305b and include trigger legs 313a and 313b flexibly, resiliently or pivotally connected to rail member rearward wall 335 to extend distally therefrom in a transverse or perpendicular direction to terminate at enlarged nubs 314a and 314b disposed in the path of longitudinal movement of barbs 319a and 319c when flange 350 is moved in response to movement of expandable portion 342 between the expanded and contracted positions. The locking and releasing mechanism 359 for locking the portal sleeve 326 in a portal sleeve or safety member retracted position where the distal end 334 of the portal sleeve is disposed proximally of penetrating member sharp tip 366 with the penetrating member in the penetrating member extended position and for releasing the portal sleeve to move to the portal sleeve or safety member extended position where distal end 334 is disposed distally of tip 366 includes a latch or locking spring 361 disposed in housing 328 and made of a strip of resilient material formed to a highly substantially flat base 363 secured to a lower wall of housing 328 or supported by structure in the housing and a bend 367 joining base 363 with an arm 369 spaced from the base. Arm 369 has an extension 377 disposed substantially parallel with the instrument longitudinal axis and carries or forms a latch 371 having an angled proximal latching surface 375 extending inwardly from extension 377 in a direction transverse or perpendicular to the longitudinal axis disposed substantially parallel with the rail member forward wall 333. A releasing or trigger member 379 is juxtaposed with extension 377 and is pivotally mounted in the housing 328 on a pin secured to a wall or walls of the housing or structure in the housing. Trigger 379 includes a leg 383 overlying extension 377 and a leg 385 extending substantially transverse from leg 383 but at a slight angle toward the proximal end of the safety penetrating instrument. A torsion spring (not shown) is coiled around the pin and fixed to trigger 379 to bias the trigger counterclockwise looking at FIG. 15 such that leg 383 is biased toward extension 377. Trigger 379 is arranged in housing 328 with leg 385 disposed in the path of longitudinal movement of barb 319c when flange 350 is moved in response to movement of expandable portion 342 between the expanded and contracted positions.

Figure 17:
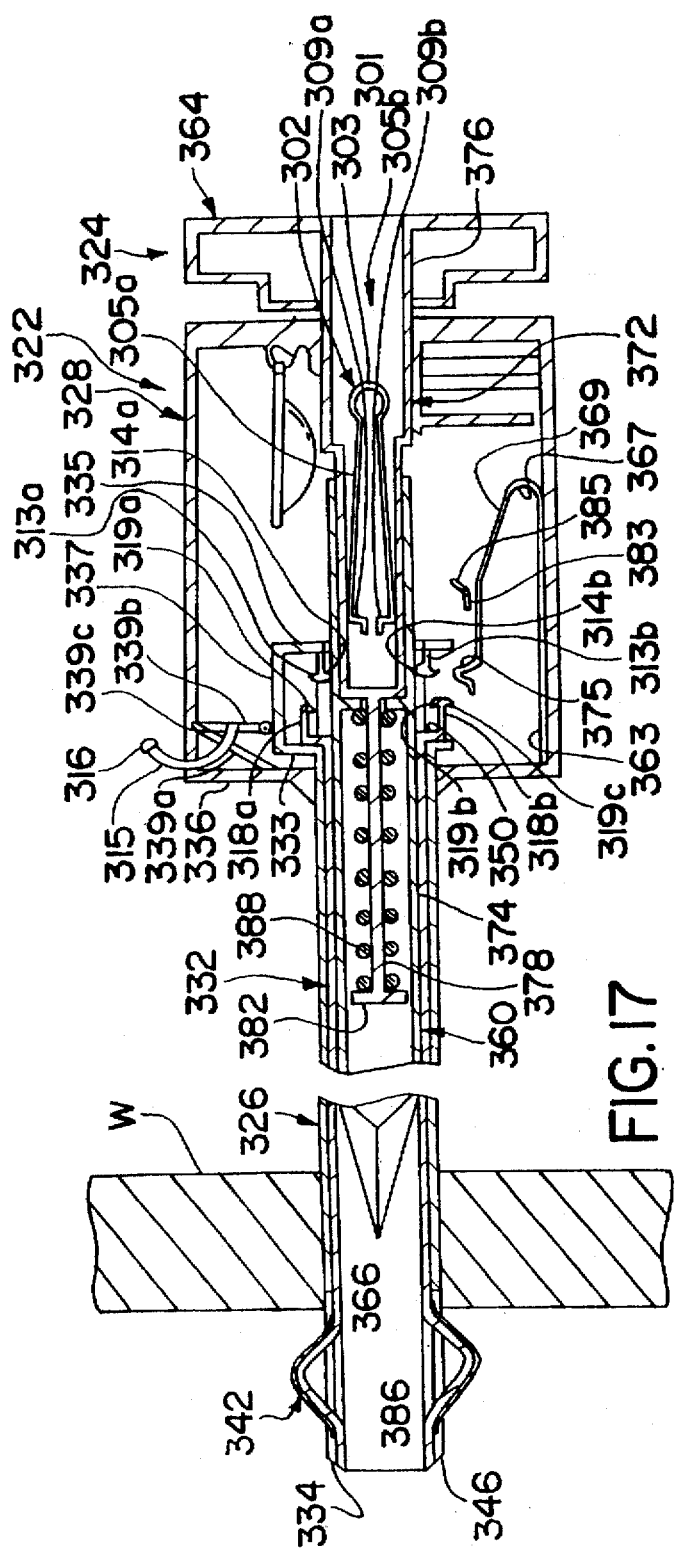
FIG. 17 is a broken side view, partly in section, of the penetrating instrument of FIG. 15 following entry in the anatomical cavity.

In use, the safety penetrating instrument 320 can be provided in the condition illustrated in FIG. 17 with the portal sleeve 326 in the portal sleeve extended position where the distal end 334 of the portal sleeve is disposed distally of sharp tip 366 and with the penetrating member 360 in the penetrating member retracted position. With the portal sleeve 326 in the portal sleeve extended position, leg 339b will be moved or pivoted around pivot 339c toward leg 339a, and curved segment 315 will extend from housing 328. Rail member 331 will be moved distally toward housing front wall 336, and the expandable portion 342 will be in the expanded position with flange 350 biased to abut rail member forward wall 333. With the penetrating member 360 in the penetrating member retracted position, distal part 374 will be moved proximally relative to end part 372 by retracting member 388. The safety penetrating instrument 320 can also be supplied with the portal sleeve 326 in the portal sleeve retracted position illustrated in FIG. 15 and with the penetrating member 360 in the penetrating member retracted position illustrated in FIG. 17 such that curved handle segment 315 does not protrude from the housing 328.

Prior to commencing penetration of an anatomical cavity wall W, the portal sleeve 326 is moved from the portal sleeve extended position to the portal sleeve retracted position by pressing button 316 to move curved segment 315 into housing 328 such that leg 339b is moved away from leg 339a. Movement of leg 339b away from leg 339a causes rail member 331 to be moved proximally until rail member forward wall 333 rides over latch 371. Once the rail member forward wall has moved proximally past latch 371, arm 369 of locking spring 361 will spring back to the normal position illustrated in FIG. 15 causing rail member forward wall 333 to be locked against latching surface 375. At this time, the portal sleeve 326 will be locked in the portal sleeve retracted position with distal end 334 disposed distally of sharp tip 366 since, at this time, the penetrating member remains in the penetrating member retracted position. With the portal sleeve locked in the portal sleeve retracted position, expandable portion 342 will remain in the expanded position with flange 350 biased to abut rail member forward wall 333, and barb 319c will be disposed distally of trigger leg 385.

When it is desired to penetrate an anatomical cavity wall W with the safety penetrating instrument 320, the handle coupled with the penetrating member distal part 374 is grasped and manually moved distally to move the distal part 374 relative to the end part 372. Once end part 372 has been moved distally past slots 308a and 308b, arms 305a and 305b will spring outwardly causing latches 309a and 309b to protrude through the slots in a normal position for locking spring 302. Distal part 374 will now be engaged by latches 309a and 309b such that the penetrating member will be locked in the penetrating member extended position with end part 372 in engagement with latching surfaces 309a and 309b. The safety penetrating instrument will now be in the condition illustrated in FIG. 15 with the penetrating member 360 locked in the penetrating member extended position where sharp tip 366 is disposed beyond the distal end 334 of the portal sleeve when the portal sleeve is locked in the portal sleeve retracted position. With the penetrating member locked in the penetrating member extended position, nubs 313a and 313b will be juxtaposed with arms 305a and 305b with barbs 314a and 314b disposed distally of nubs 313a and 313b.

During penetration of the anatomical cavity wall W, expandable portion 342 will be moved to the contracted position causing the operating member, formed by flange 350, and barbs 319a, 319b and 319c, to move proximally. As the operating member moves proximally, barbs 319a and 319b move proximally past nubs 314a and 314b without causing movement of arms 305a and 305b. Similarly, barb 319c moves proximally past trigger leg 385 without causing movement of latch 371 since there is no engagement by either leg 383 or 385 with arm extension 377. Accordingly, during penetration of the anatomical cavity wall, the portal sleeve 326 remains locked in the portal sleeve retracted position by latch 371, and the penetrating member 360 remains locked in the penetrating member extended position by latches 309a and 309b.

Figure 16:
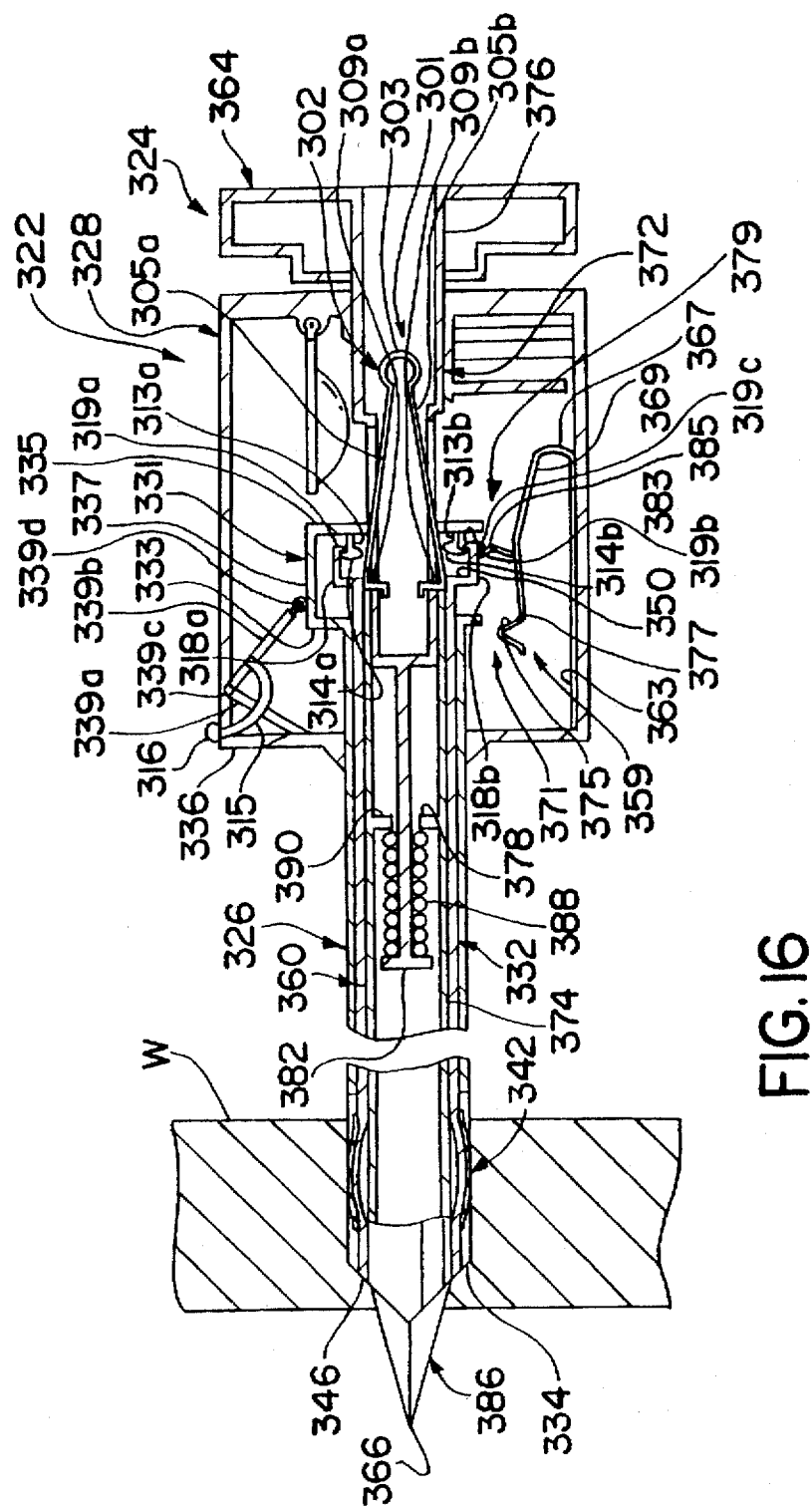
FIG. 16 is a broken side view, partly in section, of the penetrating instrument of FIG. 15 during penetration of a wall of an anatomical cavity.

Once the expandable portion 342 has been introduced in the anatomical cavity, the expandable portion will be moved to the expanded position causing the operating member to move distally. As the operating member moves distally, barbs 319a and 319b engage nubs 314a and 314b camming or pivoting trigger legs 313a and 313b inwardly in the direction of the longitudinal axis of the safety penetrating instrument. Movement of trigger legs 313a and 313b inwardly in the direction of the longitudinal axis causes nubs 314a and 314b to pivot arms 305a and 305b in the direction of the longitudinal axis to move latches 309a and 309b out of engagement with end part 372 thereby allowing retracting member 360 to move the distal part 374 of the penetrating member in a proximal direction relative to the end part 372 to the penetrating member retracted position wherein the sharp distal tip 366 is disposed within the portal sleeve. Movement of the operating member distally also causes barb 319c to engage trigger leg 385 causing the trigger 379 to pivot or rotate counterclockwise looking at FIG. 16 and causing leg 383 to engage on extension 377 moving arm 369 toward base 363 against the force of the spring strip. Movement of arm 369 away from the longitudinal axis of the safety penetrating instrument causes latch 371 to move out of engagement with rail member forward wall 333 thereby allowing extending member 341 to move the portal sleeve 326 in a distal direction to the portal sleeve extended position. Once the expandable portion is moved to the expanded position, the instrument can be pulled back toward the cavity wall until the expandable portion is adjacent or in abutment with an internal surface of the anatomical cavity wall. The enlargement formed by the expandable portion will anchor the portal sleeve relative to the anatomical cavity, and the portal sleeve will be anchored to protrude into the anatomical cavity a distance corresponding to the distance from the portal sleeve distal end to a proximal end of the expandable portion.

The safety penetrating instrument 320 provides redundant protection against inadvertent contact with tissue or organ structure and/or forming an anatomical cavity by the sharp tip of the penetrating member by providing two modes of safety: retraction of the penetrating member and protrusion of the safety member, ensuring that the sharp tip of the penetrating member will be protected even if one of the modes of safety malfunctions.

Figure 18:
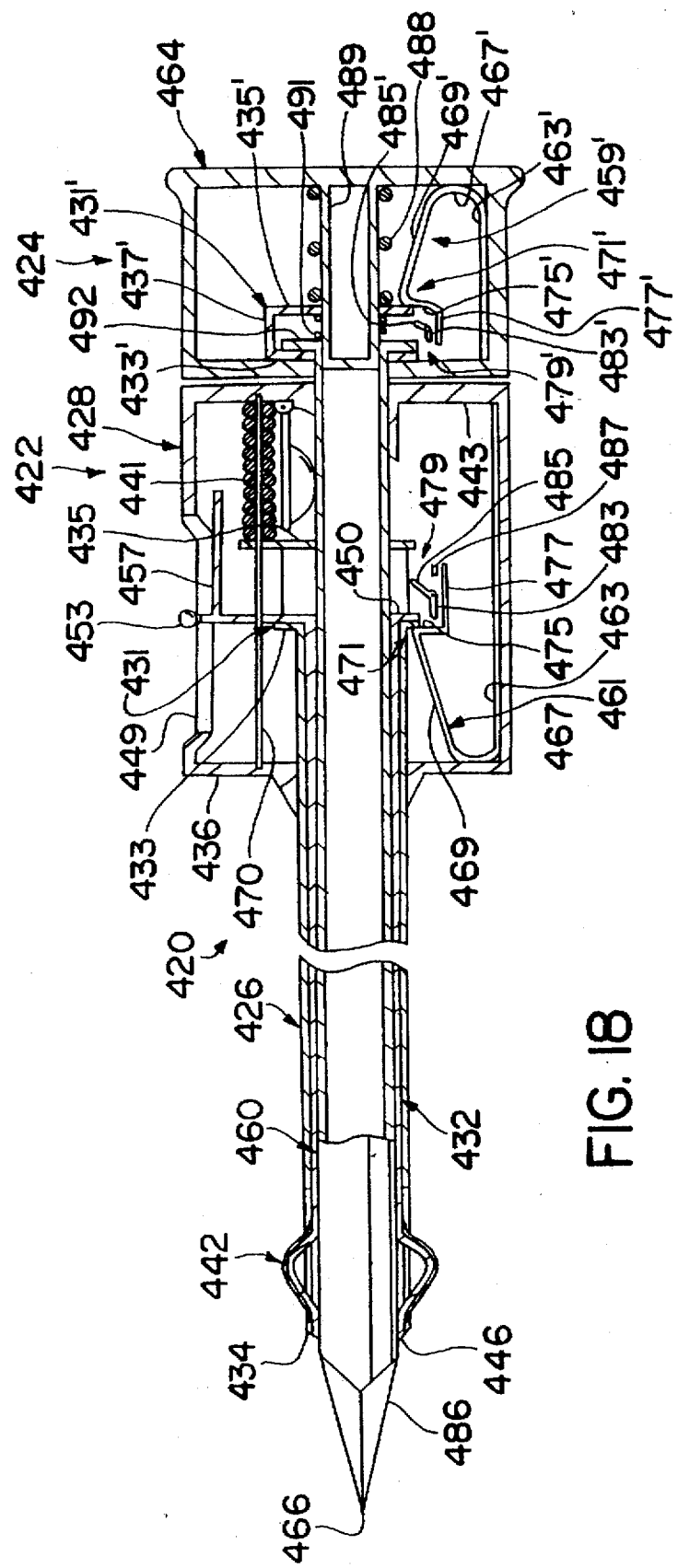
FIG. 18 is a broken side view, partly in section, of still another modification of the penetrating instrument according to the present invention.

A further embodiment of a safety penetrating instrument according to the present invention is illustrated at 420 in FIG. 18. Safety penetrating instrument 420 is similar to safety penetrating instrument 320 in that movement of expandable portion 442 of safety penetrating instrument 420 triggers both retraction of penetrating member 460 and protrusion of safety member 426; however, retractable safety penetrating instrument 420 is different in that separate, independent trigger mechanisms are provided for releasing the penetrating member to move to the penetrating member retracted position and for releasing the safety member to move to the safety member extended position. Portal unit 422 for safety penetrating instrument 420 is similar to portal unit 322 and includes portal sleeve 426 terminating proximally at a rail member 331 disposed in housing 428 and a middle member 432 terminating proximally at a flange 450 disposed between a forward wall 433 and a rearward wall 435 of the rail member. Flange 450 extends through a longitudinal slot in an upper wall of housing 428 to terminate at a knob or handle 453. An indicator strip 457 extends proximally from flange 450 in a transverse or perpendicular direction to be visible along the slot.

A locking and releasing mechanism for locking the portal sleeve in the portal sleeve retracted position and for releasing the portal sleeve to move to the portal sleeve extended position is disposed in housing 428 and includes a latch or locking spring 461 made of a strip of resilient material formed to have a substantially flat base 463 secured to a wall of housing 428 and a bend 467 joining base 463 to an upwardly angled arm 469 spaced from the base. Arm 469 carries or forms a latch 471 having an angled proximal latching surface 475 disposed substantially parallel to forward wall 433 of rail member 431. Arm 469 has an extension 477 extending proximally from latch 471, and a trigger member 479 is juxtaposed with extension 477. Trigger member 479 is similar to trigger member 379 and includes a trigger leg 483 overlying extension 477 and a trigger leg 485 extending substantially transverse from leg 483 with a slight angle toward the proximal end of the safety penetrating instrument. Trigger 479 is arranged in housing 428 with trigger leg 485 disposed in the path of longitudinal movement of flange 450 when the flange is moved in response to movement of expandable portion 442 between the expanded and contracted positions. A trigger stop 487 is mounted in housing 428, and the trigger stop can be arranged in the housing to prevent over-rotation of trigger 479 in a clockwise direction looking at FIG. 18 and to ensure proper positioning of latch 471. An extending member 441 is connected between rail member rearward wall 435 and a rear wall 443 of housing 428 to bias the portal sleeve 426 distally to the portal sleeve extended position. Extending member 441 includes a helical coil spring mounted in compression between the rail member and the housing rear wall. If desired, a guide rod 470 can be connected between the housing front wall 436 and the housing rear wall 443 with the spring being disposed concentrically around the guide rod.

Penetrating member 460 for safety penetrating instrument 420 terminates proximally at a flange 492 disposed in hub 464 with the penetrating member passing through aligned openings in the rail member forward and rearward walls 433 and 435 and in the rear wall of housing 428. A rail member 431' is disposed within hub 464 and has a generally U-shaped configuration with spaced, parallel forward and rearward walls 433' and 435', respectively, and a side wall 437' transversely connecting the forward and rearward walls. Flange 492 is disposed between the rail member forward and rearward walls 433' and 435' with the penetrating member passing through aligned openings in a forward wall of hub 464 and rail member forward wall 433'. A guide tube 489 extends distally from a rear wall of hub 464 into a proximal end of penetrating member 460 with the guide tube extending through an opening in the rail member rearward wall 435'. A bias member 491 is connected between flange 492 and the rearward wall 435' of the rail member to bias the penetrating member in a distal direction with flange 492 biased in abutment with rail member forward wall 433'. Bias member 491 is shown as a helical coil spring disposed around guide tube 489 and held in compression between flange 492 and rearward wall 435'; however, bias member 491 can include other types of springs as well as other types of bias devices. A retracting member 488 is connected between rail member rearward wall 435' and a rear wall of hub 464 to bias the penetrating member 460 to the penetrating member retracted position. As shown, the retracting member 488 includes a helical coil spring disposed around the guide tube and held in tension between the rail member rearward wall and the rear wall of the hub.

A locking and releasing mechanism 459' for locking the penetrating member in the penetrating member extended position and for releasing the penetrating member to move to the penetrating or retracted position includes a latch or locking spring 461' made of a strip of resilient material formed to have a substantially flat base 463' secured to a lower wall of hub 464 and a bend 467' joining the base with an upwardly angled arm 469'. Arm 469' carries or forms a latch 471' having a distal angled latching surface 475' disposed substantially parallel with rail member rearward wall 435', and an extension 477' of arm 469' extends distally from latch 471'. A trigger member 479' is juxtaposed with extension 477' and includes a trigger leg 483' overlying arm extension 477' and a trigger leg 485' disposed proximally of flange 492 when the penetrating member is locked in the penetrating member extended position.

Operation of safety penetrating instrument 420 is similar to that previously described in that the instrument can be provided with the portal sleeve 426 and either the portal sleeve retracted position or in the portal sleeve extended position and the penetrating member 460 and the penetrating member retracted position where sharp tip 466 is disposed proximally of a distal end 434 of the portal sleeve. When the instrument 420 is provided with the portal sleeve in the portal sleeve extended position, prior to penetration of an anatomical cavity wall, handle 453 is grasped and manually moved proximally along the slot in housing 428 to move the portal sleeve 426 to the portal sleeve retracted position with rail member forward wall 433 in engagement with latching surface 475 at which time the portal sleeve will be locked in the portal sleeve retracted position. With the portal sleeve 426 locked in the portal sleeve retracted position, expandable portion 442 will remain in the expanded position with flange 450 biased in abutment with rail member forward wall 433 and disposed distally of trigger leg 485. The penetrating member 460 is then moved to the penetrating member extended position by a handle, such as handle 453, coupled with rail member 431' or with the penetrating member 460 and movable along a longitudinal slot, such as slot 449, in hub 464. Movement of penetrating member 460 distally causes rail member 431' to bypass latch 471' until latching surface 475' engages the rail member rearward wall 435' at which time the penetrating member will be locked in the penetrating member extended position with flange 492 biased into abutment with rail member forward wall 433' and disposed distally of trigger leg 485'. The instrument will then be in the condition shown in FIG. 18 with portal sleeve 426 locked in the portal sleeve retracted position and the penetrating member 460 locked in a penetrating member extended position with sharp tip 466 disposed distally of portal sleeve distal end 434.

During penetration of an anatomical cavity wall, penetrating member 460 will be moved proximally against the bias of bias member 491 causing flange 492 to move proximally past trigger leg 485' without causing movement of latch of 471' out of engagement with rail member 431'. Expandable portion 442 at the distal end of middle member 432 will be moved to the contracted position causing flange 450 to move proximally past trigger leg 485 without causing movement of latch 471 out of engagement with rail member 431. Upon penetrating into the anatomical cavity, the penetrating member 460 will be moved distally due to the bias of bias member 491 causing flange 492 to engage trigger leg 485' and pivot trigger 479' counterclockwise, looking at FIG. 18, such that latch 471' is moved out of engagement with rail member rearward wall 435'. Accordingly, retracting member 488 will cause penetrating member 460 to move proximally to the penetrating member retracted position. Expandable portion 442 will be moved to the expanded position causing flange 450 to move distally to engage trigger leg 485 and pivot trigger 479 counterclockwise looking at FIG. 18 to move latch 471 out of engagement with rail member forward wall 433. Movement of latch 471 out of engagement with rail member 431 causes the portal sleeve to be moved distally by extending member 441 to the portal sleeve extended position.

Although the portal sleeve is disclosed herein as the safety member, it will be appreciated that the safety member can be any other member including a shield or probe. The distal bias for the safety member can be relatively strong to assure protrusion of the safety member even should the safety member engage tissue in the anatomical cavity wall or within the anatomical cavity or should any tissue be jammed between the safety member and the penetrating member. The strong distal bias for the safety member provides the surgeon with a psychological benefit of knowing the safety member is protecting the penetrating member. Should tissue within the anatomical cavity be contacted by the distal end of the safety member, the safety member can bounce or give a little in the nature of a shock absorber to protect such contacted tissue. Movement of the safety member can be seen by the surgeon by noticing movement of the handle toward a distal end of the slot and observation of the indicator strip, if provided. The strong force of the distal bias for the safety member also provides a surgeon with an easily felt tactile signal that the safety member has moved to the extended position and that penetration into the cavity has occurred which can also be visually confirmed by the position of the handle on the indicator strip. The safety member can have various configurations so long as the distal end protrudes beyond the sharp tip of the penetrating member to provide a protective function, and a plurality of safety members can be employed in the safety penetrating instrument.

The outward bias of the expandable portion and/or the distal bias of the penetrating member need only be great enough to produce slight longitudinal movement of the operating members past trigger members such that the force-to-penetrate can be minimized. With the present invention, retraction of the penetrating member can be triggered by movement of the expandable portion from a contracted position to an expanded position upon penetration through an anatomical cavity wall without requiring longitudinal movement of the penetrating member, the portal sleeve or a safety member. Movement of the expandable portion to the expanded position upon penetration through the anatomical cavity wall to trigger retraction of the penetrating member simultaneously forms an enlargement or protrusion to anchor the retractable safety penetrating instrument relative to the anatomical cavity wall. The expandable portion can be located at various locations along the retractable safety penetrating instrument to anchor the instrument relative to the anatomical cavity wall to obtain various predetermined distances of protrusion for the portal unit from the anatomical wall. Where the safety penetrating instrument is provided with a distally biased safety member, the expandable portion can be used to trigger both retraction of the penetrating member and protrusion of the safety member. Accordingly, the safety penetrating instruments according to the present invention can provide redundant safety in that two modes of safety can be provided, one relying on protrusion of the safety member and the other relying on retraction of the penetrating member to insure that the sharp tip of the penetrating member will be protected upon penetration through the anatomical cavity wall even should one of the safety modes malfunction during use. The safety and reliability of safety penetrating instruments can be further enhanced with the present invention in that separate, independent trigger mechanisms can be provided for releasing the safety member to move to the safety member extended position and for releasing the penetrating member to move to the penetrating member retracted position.

The components of the safety penetrating instrument of the present invention can be made of any suitable, medical grade materials depending upon procedural use and desirability of being disposable for single patient use or sterilizable for reuse. The components can be made of multiple parts of various configurations and materials to reduce costs. The portal unit can have various valves, stopcocks and seals in the housing to control fluid flow therethrough and various adapters to adjust to the size of the instruments inserted through the portal unit. The portal sleeve can be rigid or flexible and transparent or opaque depending on procedural use. Conventional detent mechanisms can be used to connect or lodge the housing with the hub when the portal unit and the penetrating unit are assembled. The safety member can be part of the portal unit or the penetrating unit such that the safety member can remain in place in the anatomical cavity upon withdrawal of the penetrating unit or can be withdrawn with the penetrating unit leaving only the portal sleeve in place to serve as a portal for introducing instruments into the anatomical cavity. The rail members can have various configurations to engage the latches and be released by the triggers and can have configurations to serve as a stop or abutment for the operating members.

The locking and releasing mechanisms require only a latch for locking the penetrating member in the extended position and/or a safety member in a retracted position, and a trigger for releasing the latch in response to distal movement of an operating member such as a flange carried by the penetrating member, the portal sleeve or a safety member; and, thus, it will be appreciated that various mechanisms can be employed to produce the locking and releasing functions such as, for example, multiple movably or pivotally mounted cams or pawls. It will be appreciated that the locking and releasing mechanism can be designed and arranged in the housing or the hub in various ways to minimize the length of the housing or the hub and, therefore, the overall length of the housing and hub. Various locking and releasing mechanisms that can be simply modified for use in the safety penetrating instrument of the present invention are disclosed in U.S. Pat. Nos. 5,330,432; 5,324, 268; 5,320,610; 5,336,176; and 5,360,405 to Yoon and applicant's pending applications Ser. No. 07/848,838, filed Mar. 10, 1992; Ser. No. 07/845,177, filed Sep. 15, 1992; Ser. No. 07/945,177, filed Sep. 15, 1992; Ser. No. 08/079,586, filed Jun. 22, 1993; Ser. No. 08/195,512, filed Feb. 14, 1994; Ser. No. 08/196,029, filed Feb. 14, 1994; Ser. No. 08/196, 027, filed Feb. 14, 1994; Ser. No. 08/195,178, filed Feb. 14, 1994; Ser. No. 08/237,734, filed May 4, 1994; Ser. No. 08/247,205, filed May 20, 1994; Ser. No. 08/254,007, filed Jun. 3, 1994; and Ser. No. 08/260,439, filed Jun. 15, 1994. The disclosures of the above-listed issued patents and pending patent applications are incorporated herein by reference. The issued patents and pending applications listed above also disclose various bias arrangements useful with the safety penetrating instrument of the present invention. Other locking and releasing mechanisms that can be used in the safety penetrating instrument of the present invention are disclosed in applicant's pending applications Ser. Nos. 08/279,170 and 08/279,172, filed Jul. 22, 1994, the disclosures of which are incorporated herein by reference.

One or more control buttons, such as the control buttons described in applicant's copending patent application, Ser. No. 08/083,220, filed Jun. 24, 1993, can be mounted next to any latch for manually disengaging the latch to prevent locking of the penetrating member in the extended position and/or the portal sleeve in a retracted position. Furthermore, additional latches can be provided or existing latches modified to carry pawls or form latching surfaces for locking a penetrating member in the retracted position and/or a safety member in the extended position, and such latches can then be released through the use of control buttons as described above to permit the penetrating member and/or safety member to be moved prior to use.

The distal end of the penetrating member for the safety penetrating instrument of the present invention can have any configuration desired for a particular procedure, for example, the pyramidal trocar configuration shown or a conical distal end 586 tapering from a junction 593 to a tip 566 as shown in FIG. 19, a beveled distal end 686 tapering from a junction 693 to a tip 666 as shown in FIG. 20, a screw-type distal end 786 having helical threads 797 as shown in FIG. 21, a multi-faceted distal end 886 having two or more facets 897 tapering from a junction 893 to a tip 866 as shown in FIG. 22, a blunt distal end 986 of generally conical configuration terminating in a rounded or flattened tip 966 as shown in FIG. 23, or a hollow tubular needle-like configuration with a beveled distal end 1086 tapering from a junction 1093 to a sharp tip 1066 and defining a lumen to permit the flow of fluid therethrough and/or to accommodate a safety probe disposed therein as shown in phantom in FIG. 24. Additionally, the surface defining the distal end of the penetrating member can be irregular or smooth, continuous or disjointed, provided with cutting features or having any combination of the above. Any of the penetrating members shown and described herein can include a viewing port, like the viewing port shown in phantom at 1195 in FIG. 19, for accommodating conventional optical viewing systems such as those utilizing fiber optics so that tissue can be visualized during penetration. It will also be appreciated that the distal end of the portal sleeve can be proximally spaced, distally spaced or aligned with the penetrating member junction from which the distal end extends prior to penetrating an anatomical cavity wall, for example when the penetrating member is locked in an extended position and/or the portal sleeve is locked in a retracted position.

From the above, it will be appreciated that the penetrating instrument of the present invention allows the distal end of a portal sleeve to be automatically anchored relative to an anatomical cavity wall without intervention by a surgeon and without requiring complex mechanisms or parts. With the penetrating instrument of the present invention, automatic anchoring is achieved through the use of an expandable portion movable between expanded and contracted positions in response to resistance from anatomical tissue during penetration of an anatomical cavity wall and a reduction in tissue resistance following entry into the anatomical cavity. It will be further appreciated that the penetrating instrument of the present invention permits use of a safety member and strong bias springs to assure movement of the safety member to the extended protruding position without increasing the force-to-penetrate and without longitudinal movement of the portal sleeve and the penetrating member. After penetration of the penetrating instrument into the anatomical cavity, the safety member can act as a shock absorber upon inadvertent contact with tissue which contact can be felt by the surgeon and visually determined by movement of the handle. Movement of the safety member to the extended protruding position and/or movement of the penetrating member to the protective retracted position can be triggered by transverse expansion of an expandable portion of the penetrating instrument automatically upon penetration into the anatomical cavity, and expansion of the expandable portion will simultaneously anchor the penetrating instrument relative to the anatomical cavity. The features of the various embodiments described above can be combined in any manner desired dependent upon the requirements and complexity of the penetrating instruments.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A penetrating instrument for penetrating an anatomical cavity wall to gain access to an anatomical cavity comprising a cannula having a distal end for being disposed in the anatomical cavity and a proximal end for being disposed externally of the anatomical cavity;

a penetrating member disposed in said cannula and having a distal end for penetrating the anatomical cavity wall;

a middle member disposed between said cannula and said penetrating member, said middle member having a distal end and a longitudinal axis; and an expandable portion disposed along said middle member a predetermined distance from said middle member distal end, said expandable portion being biased outwardly in a lateral direction transverse to said longitudinal axis to an expanded position and being movable to a contracted position against said bias during penetration of the anatomical cavity wall to facilitate introduction of said cannula distal end in the anatomical cavity, said expandable portion further being movable from said contracted position to said expanded position upon introduction of said expandable portion in the anatomical cavity to anchor said cannula to protrude into the anatomical cavity a distance corresponding to said predetermined distance;

wherein said expandable portion includes a plurality of strips extending longitudinally along said middle member and biased in a direction transverse to said longitudinal axis to be disposed outwardly of said middle member in said expanded position and wherein said cannula includes a plurality of slots aligned with said strips to allow passage therethrough by said strips in said expanded position.

2. A safety penetrating instrument for penetrating an anatomical cavity wall to gain access to an anatomical cavity comprising a penetrating member having a longitudinal axis and a distal end for penetrating the anatomical cavity wall;

a safety member having a distal end and being movable relative to said penetrating member between an extended position where said safety member distal end protrudes distally from said penetrating member distal end and a retracted position where said safety member distal end is disposed proximally of said penetrating member distal end to expose said penetrating member distal end;

extending means for moving said safety member distally to said extended position; and for permitting said safety member to move proximally to said retracted position;

handle means coupled with said safety member for manually moving said safety member proximally to said retracted position;

locking means for locking said safety member in said retracted position during penetration of the anatomical cavity wall;

an expandable portion carried by said safety penetrating instrument and being movable inwardly in a lateral direction transverse to said longitudinal axis from an expanded position to a contracted position during penetration of the anatomical cavity wall and outwardly in the lateral direction from said contracted position to said expanded position upon introduction of said expandable portion in the anatomical cavity;

releasing means responsive to movement of said expandable portion from said contracted position to said expanded position for triggering release of said locking means to permit said extending means to move said safety member to said extended position; and an operating member coupled with said expandable portion for being moved proximally in response to movement of said expandable portion from said expanded position to said contracted position and for being moved distally to trigger release of said locking means in response to movement of said expandable portion from said contracted position to said expanded position.

3. A safety penetrating instrument as recited in claim 2 wherein said expandable portion includes at least one strip extending longitudinally along said penetrating instrument.

4. A safety penetrating instrument as recited in claim 3 and further including a flexible membrane disposed over said at least one strip.

5. A safety penetrating instrument as recited in claim 3 wherein said safety member includes a portal sleeve receiving said penetrating member.

6. A safety penetrating instrument as recited in claim 5 and further including a middle member disposed in said portal sleeve and wherein said expandable portion includes a plurality of spring strips extending longitudinally along said middle member and said portal sleeve includes a plurality of longitudinally extending slots aligned with said spring strips to allow passage therethrough by the spring strips in said expanded position.

7. A safety penetrating instrument as recited in claim 6 wherein said middle member includes a distal end secured to said safety member distal end and said middle member is movable longitudinally by said spring strips in response to movement of said expandable portion between said expanded and contracted positions.

8. A safety penetrating instrument as recited in claim 7 wherein said middle member includes a proximal end and said operating member is disposed at said proximal end of said middle member.

9. A safety penetrating instrument for penetrating an anatomical cavity wall to gain access to an anatomical cavity comprising a cannula having a distal end for being disposed in the anatomical cavity and a proximal end for being disposed externally of the anatomical cavity;

a penetrating member disposed within said cannula and having a distal end for penetrating the anatomical cavity wall, said penetrating member having a longitudinal axis and being movable relative to said cannula between an extended position where said distal end of said penetrating member protrudes distally from said distal end of said cannula and a retracted position proximally spaced from said extended position;

retracting means for moving said penetrating member proximally from said extended position to said retracted position and for permitting said penetrating member to move distally to said extended position;

handle means coupled with said penetrating member for manually moving said penetrating member distally to said extended position;

locking means for locking said penetrating member in said extended position during penetration of the anatomical cavity wall;

an expandable portion carried by said safety penetrating instrument and movable inwardly in a lateral direction transverse to said longitudinal axis from an expanded position to a contracted position during penetration of the anatomical cavity wall and outwardly in the lateral direction from said contracted position to said expanded position upon introduction of said expandable portion in the anatomical cavity;

releasing means responsive to movement of said expandable portion from said contracted position to said expanded position for triggering release of said locking means to permit said retracting means to move said penetrating member to said retracted position; and an operating member coupled with said expandable portion for being moved proximally in response to movement of said expandable portion from said expanded position to said contracted position and for being moved distally to trigger release of said locking means in response to movement of said expandable portion from said contracted position to said expanded position.

10. A safety penetrating instrument as recited in claim 9 wherein said expandable portion includes at least one strip extending longitudinally along said penetrating instrument.

11. A safety penetrating instrument as recited in claim 10 and further including a flexible membrane disposed over said at least one strip.

12. A safety penetrating instrument as recited in claim 10 and further including a middle member disposed in said cannula and wherein said expandable portion includes a plurality of spring strips extending longitudinally along said middle member and said cannula includes a plurality of longitudinally extending slots aligned with said spring strips to allow passage therethrough by the spring strips in said expanded position.

13. A safety penetrating instrument as recited in claim 12 wherein said middle member includes a distal end secured to said cannula distal end and said middle member is movable longitudinally by said spring strips in response to movement of said expandable portion between said expanded and contracted positions.

14. A safety penetrating instrument as recited in claim 13 wherein said middle member includes a proximal end and said operating member is disposed at said proximal end of said middle member.

15. A safety penetrating instrument for penetrating an anatomical cavity wall to gain access to an anatomical cavity comprising a housing;

a cannula having a proximal end mounted by said housing and a distal end for introduction in the anatomical cavity, said cannula being movable relative to said housing between an extended protruding position and a proximally spaced retracted position;

a penetrating member disposed in said cannula and having a distal end for penetrating the anatomical wall, said penetrating member being movable relative to said cannula between an extended position where said distal end of said penetrating member protrudes distally from said distal end of said retracted cannula and a retracted position where said distal end of said penetrating member is proximally spaced from said distal end of said extended cannula;

extending means for moving said cannula distally to said cannula extended position and for permitting said cannula to move proximally to said cannula retracted position;

retracting means for moving said penetrating member proximally to said penetrating member retracted position and for permitting said penetrating member to move distally to said penetrating member extended position;

cannula locking means for locking said cannula in said cannula retracted position during penetration of the anatomical cavity wall;

penetrating member locking means for locking said penetrating member in said penetrating member extended position during penetration of the anatomical cavity wall;

an expandable portion carried by said safety penetrating instrument and movable inwardly in a lateral direction transverse to a longitudinal axis of said instrument from an expanded position to a contracted position during penetration of the anatomical cavity wall and outwardly in the lateral direction from said contracted position to said expanded position upon introduction of said expandable portion in the anatomical cavity;

releasing means responsive to movement of said expandable portion from said contracted position to said expanded position for triggering release of said locking means to permit said extending means to move said cannula to said extended position and said retracting means to move said penetrating member to said retracted position; and an operating member coupled with said expandable portion for being moved proximally in response to movement of said expandable portion from said expanded position to said contracted position and for being moved distally to trigger release of said locking means in response to movement of said expandable portion from said contracted position to said expanded position.

16. A safety penetrating instrument as recited in claim 15 wherein said expandable portion includes at least one strip extending longitudinally along said penetrating instrument.

17. A safety penetrating instrument as recited in claim 16 and further including a flexible membrane disposed over said at least one strip.

18. A safety penetrating instrument as recited in claim 16 wherein said safety member includes a portal sleeve receiving said penetrating member.

19. A safety penetrating instrument as recited in claim 18 and further including a middle member disposed in said cannula and wherein said expandable portion includes a plurality of spring strips extending longitudinally along said middle member and said cannula includes a plurality of longitudinally extending slots aligned with said spring strips to allow passage therethrough by the spring strips in said expanded position.

20. A safety penetrating instrument as recited in claim 19 wherein said middle member includes a distal end secured to said safety member distal end and said middle member is movable longitudinally by said spring strips in response to movement of said expandable portion between said expanded and contracted positions.

21. A safety penetrating instrument as recited in claim 20 wherein said middle member includes a proximal end and said operating member is disposed at said proximal end of said middle member.

* * * * *